(12) United States Patent
Marek et al.

US006762202B2

(10) Patent No.: US 6,762,202 B2
(45) Date of Patent: Jul. 13, 2004

(54) INFRARED THERMOGRAPHY AND METHODS OF USE

(75) Inventors: Przemyslaw A. Marek, Bolton, MA (US); Andzrej M. Trocha, Billerica, MA (US); Chia-En Lin, Burlington, MA (US); Ramani R. Ranatunga, Lexington, MA (US); Stewart K. Richardson, Tolland, CT (US)

(73) Assignee: NitroMed, Inc., Bedford, MA (US)

(*) Notice: Subject to any disclaimer, the term of this patent is extended or adjusted under 35 U.S.C. 154(b) by 0 days.

(21) Appl. No.: 09/850,081

(22) Filed: May 8, 2001

(65) Prior Publication Data

US 2001/0046471 A1 Nov. 29, 2001

Related U.S. Application Data

(60) Provisional application No. 60/202,935, filed on May 9, 2000.

(51) Int. Cl.[7] .................. A01N 47/40; A01N 47/46; A01N 47/48; A01N 31/21; A01N 31/26
(52) U.S. Cl. .................. 514/515; 514/560; 514/608; 514/613; 514/929; 424/78.03
(58) Field of Search .................. 424/9.2, 9.8, 400, 424/78.03, 78.02; 514/515, 608, 613, 560, 929

(56) References Cited

U.S. PATENT DOCUMENTS

| 5,340,586 A | 8/1994 | Pike et al. |
|---|---|---|
| 5,371,107 A | 12/1994 | Hotzel et al. |
| 5,380,757 A | 1/1995 | Horrobin |
| 5,380,758 A | 1/1995 | Stamler et al. |
| 5,565,466 A | 10/1996 | Gioco et al. |
| 5,574,068 A | 11/1996 | Stamler et al. |
| 5,648,393 A | 7/1997 | Stamler et al. |
| 5,666,962 A | 9/1997 | Lamey |
| 5,698,589 A | 12/1997 | Allen |
| 5,877,216 A | 3/1999 | Place et al. |
| 5,891,915 A | 4/1999 | Wysor et al. |
| 5,906,636 A * | 5/1999 | Casscells et al. .............. 607/96 |
| 5,908,853 A | 6/1999 | Nahoum |
| 5,952,361 A | 9/1999 | Dias Nahoum |
| 5,993,856 A | 11/1999 | Ragavan et al. |
| 5,994,363 A | 11/1999 | El-Rashidy et al. |
| 6,017,521 A | 1/2000 | Robinson et al. |
| 6,031,002 A | 2/2000 | Wysor et al. |
| 6,036,977 A | 3/2000 | Drizen et al. |
| 6,132,757 A | 10/2000 | Cutler |
| 6,165,975 A | 12/2000 | Adams et al. |
| 6,193,992 B1 | 2/2001 | El-Rashidy et al. |
| 6,214,374 B1 | 4/2001 | Schmirler et al. |
| 6,245,819 B1 | 6/2001 | Halonen et al. |
| 6,251,436 B1 | 6/2001 | Drizen et al. |
| 6,258,373 B1 | 7/2001 | Cutler |
| 6,277,884 B1 | 8/2001 | de Tejada |
| 6,294,517 B1 | 9/2001 | Garvey et al. |
| 6,306,841 B1 | 10/2001 | Place et al. |
| 6,316,501 B1 * | 11/2001 | Miyamoto .................. 514/562 |
| 6,323,211 B1 | 11/2001 | Garvey et al. |
| 2001/0039257 A1 * | 11/2001 | Adams et al. .................. 514/2 |
| 2002/0019349 A1 * | 2/2002 | Conrad et al. ................ 514/12 |
| 2002/0028846 A1 * | 3/2002 | Yeager et al. ............... 514/513 |

FOREIGN PATENT DOCUMENTS

| WO | WO99/10731 | 3/1999 |
|---|---|---|
| WO | WO99/20266 A1 | 4/1999 |
| WO | WO99/60630 | 11/1999 |

OTHER PUBLICATIONS

Seeley et al., Archives of Sexual Behavior; 9 (2): 77–85 (1980).

* cited by examiner

*Primary Examiner*—Sreeni Padmanabhan
*Assistant Examiner*—Lauren Q. Wells
(74) *Attorney, Agent, or Firm*—Hale and Dorr LLP

(57) ABSTRACT

The present invention describes rapid noninvasive methods for measuring vasodilation or changes in blood flow in a patient following administration of at least one compound that donates, transfers or releases nitric oxide, elevates endogenous levels of endothelium-derived relaxing factor, stimulates endogenous synthesis of nitric oxide or is a substrate for nitric oxide synthase and/or at least one vasoactive agent. The method comprises the administration of at least one compound that donates, transfers or releases nitric oxide, elevates endogenous levels of endothelium-derived relaxing factor, stimulates endogenous synthesis of nitric oxide or is a substrate for nitric oxide synthase and/or at least one vasoactive agent to the patient followed by monitoring the temperature change of an area of interest using infrared thermography. The present invention provides methods for diagnosing diseases or disorders related to vasodilation and changes in blood flow, such as, sexual dysfunction, Raynaud's syndrome, inflammation, hypertension, gastrointestinal disorders and central nervous system disorders. The sexual dysfunction is preferably female sexual dysfunction and female sexual arousal. The vasoactive agents include potassium channel activators, calcium channel blockers, α-adrenergic receptor antagonists, β-blockers, phosphodiesterase inhibitors, adenosine, ergot alkaloids, vasoactive intestinal peptides, prostaglandins, dopamine agonists, opioid antagonists, endothelin antagonists and thromboxane inhibitors. The present invention can also be used to screen and identify drug candidates for treating diseases, disorders and conditions resulting from vasodilation or changes in blood flow. The present invention also describes compositions comprising at least one S-nitrosothiol compound for diagnosing, monitoring and/or treating female sexual dysfunctions.

15 Claims, 6 Drawing Sheets

(4 of 6 Drawing Sheet(s) Filed in Color)

INFRARED THERMOGRAPHY AND METHODS OF USE

RELATED APPLICATIONS

This application claims priority to U.S. Provisional Application No. 60/202,935 filed May 9, 2000.

FIELD OF THE INVENTION

The present invention describes rapid noninvasive methods for measuring vasodilation or changes in blood flow in a patient following administration of at least one compound that donates, transfers or releases nitric oxide, elevates endogenous levels of endothelium-derived relaxing factor, stimulates endogenous synthesis of nitric oxide or is a substrate for nitric oxide synthase and/or at least one vasoactive agent. The method comprises the administration of at least one compound that donates, transfers or releases nitric oxide, elevates endogenous levels of endothelium-derived relaxing factor, stimulates endogenous synthesis of nitric oxide or is a substrate for nitric oxide synthase and/or at least one vasoactive agent to the patient followed by monitoring the temperature change of an area of interest using infrared thermography. The present invention provides methods for diagnosing diseases or disorders related to vasodilation and changes in blood flow, such as, sexual dysfunctions, Raynaud's syndrome, inflammation, hypertension, gastrointestinal disorders and central nervous system disorders. The sexual dysfunction is preferably female sexual dysfunction or female sexual arousal. The vasoactive agents include potassium channel activators, calcium channel blockers, α-adrenergic receptor antagonists, β-blockers, phosphodiesterase inhibitors, adenosine, ergot alkaloids, vasoactive intestinal peptides, prostaglandins, dopamine agonists, opioid antagonists, endothelin antagonists and thromboxane inhibitors. The present invention can also be used to screen and identify drug candidates for treating diseases, disorders and conditions resulting from vasodilation or changes in blood flow. The present invention also describes compositions comprising at least one S-nitrosothiol compound for diagnosing, monitoring and/or treating female sexual dysfunctions.

BACKGROUND OF THE INVENTION

Adequate sexual function is a complex interaction of hormonal events and psychosocial relationships. There are four stages to sexual response as described in the *International Journal of Gynecology & Obstetrics*, 51(3):265–277 (1995). The first stage of sexual response is desire. The second stage of sexual response is arousal. Both physical and emotional stimulation may lead to breast and genital vasodilation and clitoral engorgement (vasocongestion). In the female, dilation and engorgement of the blood vessels in the labia and tissue surrounding the vagina produce the "orgasmic platform," an area at the distal third of the vagina where blood becomes sequestered. Localized perivaginal swelling and vaginal lubrication make up the changes in this stage of sexual response. Subsequently, ballooning of the proximal portion of the vagina and elevation of the uterus occurs. In the male, vasodilation of the cavemosal arteries and closure of the venous channels that drain the penis produce an erection. The third stage of sexual response is orgasm, while the fourth stage is resolution. Interruption or absence of any of the stages of the sexual response cycle can result in sexual dysfunction. One study found that 35% of males and 42% of females reported some form of sexual dysfunction. Read et al, *J. Public Health Med.*, 19(4):387–391 (1997).

While there are obvious differences in the sexual response between males and females, one common aspect of the sexual response is the erectile response. The erectile response in both males and females is the result of engorgement of the erectile tissues of the genitalia with blood which is caused by the relaxation of smooth muscles in the arteries serving the genitalia. This increase in blood flow results in vasodilation and an increase in the temperature of the genitalia tissue.

Methods for evaluating and measuring physiological changes to determine sexual arousal have been previously described. For example, U.S. Pat. Nos. 5,565,466 and 5,731,339 describe the use of Doppler ultrasound velocimetry for measuring vaginal and penile blood flow; *Intl. J. Impotence Res.*, 9:27–37 (1997) discloses the use of photoplethysmorgraphy for monitoring vaginal blood flow; and WO 99/35968 describes devices and methods for monitoring female arousal. These prior art methods are invasive and have major limitations that can effect the accuracy of the measurements.

There is a need in the art for new and improved noninvasive methods for measuring vasodilation and changes in blood flow, and for diagnosing and monitoring diseases related to vasodilation, such as, sexual dysfunctions. The present invention is directed to these, as well as other, important ends.

SUMMARY OF THE INVENTION

In arriving at the present invention, it was unexpectedly discovered that the vasodilation or engorgement of the corpus cavemosum smooth muscle, an event involved in the sexual response process in both males and females, results in an increase in temperature that can be monitored by infrared thermography.

One aspect of the present invention describes methods for monitoring and measuring vasodilation and changes in blood flow in patients, by administering to a patient in need thereof at least one compound that donates, transfers or releases nitric oxide, elevates endogenous levels of endothelium-derived relaxing factor, stimulates endogenous synthesis of nitric oxide or is a substrate for nitric oxide synthase and/or at least one vasoactive agent, followed by monitoring the temperature change of an area of interest using infrared thermography. Another aspect of the invention comprises the steps of comparing the temperature of the area prior to and after the administration of the nitric oxide donor and/or vasoactive agent. Thus the method may comprise (i) measuring the baseline temperature of an area of interest before exposure to at least one nitric oxide donor and/or vasoactive agent using infrared thermography, (ii) administering to a patient at least one nitric oxide donor and/or vasoactive agent, (iii) measuring the temperature of the area of interest during and/or after administering of at least one nitric oxide donor and/or vasoactive agent using infrared thermography, and (iv) comparing the measurements obtained in steps (i) and (iii), wherein a compound that results in an increase in the temperature is a vasodilator and a compound that results in a decrease in the temperature is a vasoconstrictor. The temperature in step (i) may be a previously obtained stable temperature measurement; or alternatively a measurement taken any time after the administration of the nitric oxide donor and/or vasoactive agent when a stable temperature measurement is obtained. The nitric oxide donors, and/or vasoactive agents can be administered separately or as components of the same composition in one or more pharmaceutically acceptable carriers.

Another aspect of the invention provides methods for monitoring and diagnosing diseases and disorders related to blood flow, such as, sexual dysfunctions and sexual arousal in patients, preferably males and females, more preferably females, by administering to a patient in need thereof at least one compound that donates, transfers or releases nitric oxide, elevates endogenous levels of endothelium-derived relaxing factor, stimulates endogenous synthesis of nitric oxide or is a substrate for nitric oxide synthase and/or at least one vasoactive agent, followed by measuring the temperature of the genitalia using infrared thermography or followed by comparing the temperature of the genitalia after administration of the at least one nitric oxide donor and/or vasoactive agent with a stable baseline temperature measurement obtained using infrared thermography.

Yet another aspect of the invention provides methods for monitoring and diagnosing diseases and disorders resulting from vasodilation and changes in blood flow by administering to a patient in need thereof at least one compound that donates, transfers or releases nitric oxide, elevates endogenous levels of endothelium-derived relaxing factor, stimulates endogenous synthesis of nitric oxide or is a substrate for nitric oxide synthase and/or at least one vasoactive agent, followed by comparing the temperature change of the area of interest after administration of the at least one nitric oxide donor and/or vasoactive agent with a stable baseline temperature measurement using infrared thermography. The diseases and disorders resulting from changes in blood flow include Raynaud's syndrome, inflammation, hypertension, gastrointestinal disorders and central nervous system disorders.

Another aspect of the present invention comprises identification, characterization, rank and selection of compounds that are can be used to treat numerous diseases and disorders resulting from vasodilation and changes in blood flow. For example a test compound may be administered to a patient followed by infrared thermographic measurements of an area of interest to monitor the temperature changes. Compounds that result in a temperature increase are effective for the treatment of the disease or disorder, the greater the increase in temperature, the more potent the compound as a suitable therapy. On the other hand, compounds that produce no temperature change or that result in a temperature decrease are not effective for the treatment of the disease or disorder, the greater the decrease in temperature, the less effective the compound as a suitable therapy.

Yet another aspect of the present invention provides compositions comprising at least one S-nitrosothiol compound and at least one penetration enhancer that may be used to diagnose, monitor and/or treat female sexual dysfunctions. The S-nitrosothiol compound may preferably be S-nitrosoglutathione. The penetration enhancer, may preferably be a glyceride, such as, MIGLYOL® and/or a polyglycolyzed glyceride, such as, LABROSOL® and/or LABROFIL®, or a mixture thereof. These compositions may further comprise at least one vasoactive agent and/or at least one nitric oxide donor, or mixtures thereof.

These and other aspects of the present invention are described in detail herein.

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
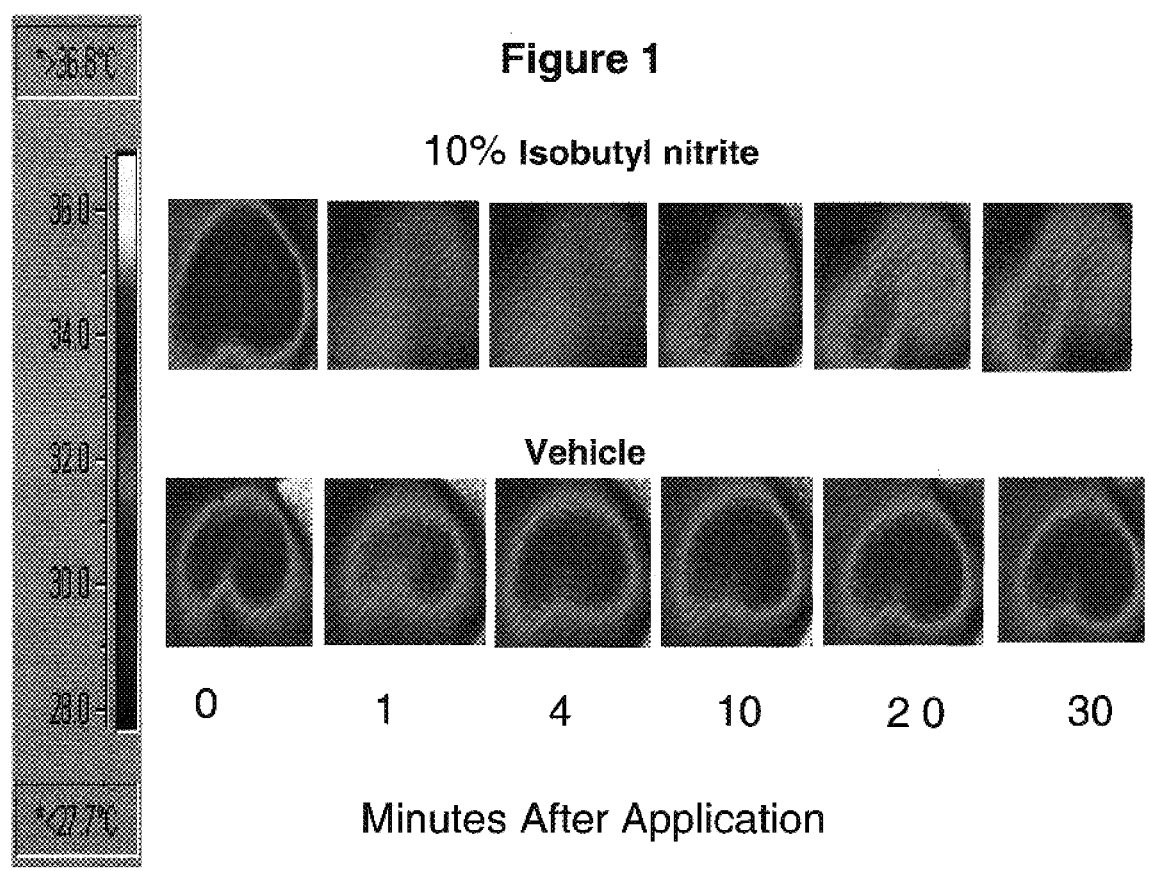
FIG. 1 shows the infrared thermographic images following topical administration of 10% isobutryl nitrate (top panels) or vehicle (bottom panels) to a rabbit vagina and clitoris. The x axis corresponds to time in minutes from just prior to application of isobutryl nitrate or vehicle (0 minutes) to 30 minutes after application of isobutryl nitrate or vehicle. The vertical bar on the left hand side corresponds to the color change for temperatures ranging from 28° C. to 36° C.

As used throughout the disclosure, the following terms, unless otherwise indicated, shall be understood to have the following meanings.

"Patient" refers to animals, preferably mammals, more preferably humans, and includes children and adults, and males and females.

"Infrared thermography" refers to the recording of the temperature of a body by means of infrared radiation emitted by the surface of the body at wavelengths of between about 0.8 $\mu$m and about 1 mm. The monitoring of radiation is preferably in the range of about 3 $\mu$m to about 100 $\mu$m, more preferably in the range of about 3 $\mu$m to about 15 $\mu$m, and most preferably in the range of about 3 $\mu$m to about 12 $\mu$m.

"Area of interest" refers to the area whose temperature is recorded and monitored using infrared thermography. The area of interest may include the symptomatic area.

"Baseline temperature" refers to the temperature of the area of interest at rest i.e., without the administration of a compound. The baseline temperature can be measured at, for example, prior to the administration of the test compound i.e., nitric oxide donor and/or vasoactive agent. Alternatively, the baseline temperature can be measured after the administration of the nitric oxide donor and/or vasoactive agent when a stable temperature reading is obtained.

"Vasoactive agent" refers to any therapeutic agent capable of relaxing vascular and/or nonvascular smooth muscle. Suitable vasoactive agents include, but are not limited to, potassium channel activators, calcium channel blockers, β-blockers, long and short acting α-adrenergic receptor antagonists, prostaglandins, phosphodiesterase inhibitors, adenosine, ergot alkaloids, vasoactive intestinal peptides, dopamine agonists, opioid antagonists, endothelin antagonists, thromboxane inhibitors, and the like.

"Thromboxane inhibitor" refers to any compound that reversibly or irreversibly inhibits thromboxane synthesis, and includes compounds which are the so-called thromboxane $A_2$ receptor antagonists, thromboxane $A_2$ antagonists, thromboxane $A_2$/prostaglandin endoperoxide antagonists, thromboxane receptor (TP) antagonists, thromboxane antagonists, thromboxane synthase inhibitors, and dual acting thromboxane synthase inhibitors and thromboxane receptor antagonists.

"Thromboxane $A_2$ receptor antagonist" refers to any compound that reversibly or irreversibly blocks the activation of any thromboxane $A_2$ receptor.

"Thromboxane synthase inhibitor" refers to any compound that reversibly or irreversibly inhibits the enzyme thromboxane synthesis thereby reducing the formation of thromboxane $A_2$.

"Dual acting thromboxane receptor antagonist and thromboxane synthase inhibitor" refers to any compound that simultaneously acts as a thromboxane $A_2$ receptor antagonist and a thromboxane synthase inhibitor.

"Raynaud's syndrome" refers to a condition that causes a loss of blood flow to the fingers, toes, nose and/or ears. The affected area turns white from the lack of circulation, then blue and cold, and finally numb. The affected area may also turn red, and may throb, tingle or swell.

"Gastrointestinal disorder" refers to any disease or disorder of the upper gastrointestinal tract of a patient including, for example, inflammatory bowel disease, peptic ulcers, stress ulcers, gastric hyperacidity, dyspepsia, gastroparesis, Zollinger-Ellison syndrome, gastroesophageal reflux disease, short-bowel (anastomosis) syndrome, hypersecretory states associated with systemic mastocytosis or basophilic leukemia and hyperhistaminemia, and bleeding peptic ulcers that result, for example, from neurosurgery, head injury, severe body trauma or burns.

"Upper gastrointestinal tract" refers to the esophagus, the stomach, the duodenum and the jejunum.

"Ulcers" refers to lesions of the upper gastrointestinal tract lining that are characterized by loss of tissue. Such ulcers include gastric ulcers, duodenal ulcers and gastritis.

"Therapeutically effective amount" refers to the amount of the compound and/or composition that is effective to achieve its intended purpose.

"Topical" refers to the delivery of a compound by passage through the skin and into the blood stream and includes transdermal delivery.

"Transdermal" refers to the delivery of a compound by passage through the skin and into the blood stream.

"Transmucosal" refers to delivery of a compound by passage of the compound through the mucosal tissue and into the blood stream.

"Penetration enhancement" or "permeation enhancement" refers to an increase in the permeability of the skin or mucosal tissue to a selected pharmacologically active compound such that the rate at which the compound permeates through the skin or mucosal tissue is increased.

"Vaginal delivery" refers to the direct administration of a pharmaceutical composition to the vagina of the patient. Generally, "vaginal delivery" of a pharmaceutical composition involves administration to the distal several centimeters of the vagina.

"Vulvar delivery" or "vulvar administration" to refer to application of a pharmaceutical composition to the vulvar area of a patient. The term is intended to encompass application to the clitoris as well as the surrounding vulvar area. The terms "vulvar delivery" and "clitoral delivery" are used interchangeably herein and are both intended to refer to administration to the vulvar area of the patient.

"Carriers" or "vehicles" refers to carrier materials suitable for compound administration and include any such material known in the art such as, for example, any liquid, gel, solvent, liquid diluent, solubilizer, or the like, which is non-toxic and which does not interact with any components of the composition in a deleterious manner.

"Sustained release" refers to the release of a therapeutically active compound and/or composition such that the blood levels of the therapeutically active compound are maintained within a desirable therapeutic range over an extended period of time. The sustained release formulation can be prepared using any conventional method known to one skilled in the art to obtain the desired release characteristics.

"Nitric oxide donor" or "NO donor" refers to compounds that donate, release and/or directly or indirectly transfer a nitrogen monoxide species, and/or stimulate the endogenous production of nitric oxide or endothelium-derived relaxing factor (EDRF) in vivo and/or elevate endogenous levels of nitric oxide or EDRF in vivo. "NO donor" also includes compounds that are substrates for nitric oxide synthase.

"Nitric oxide adduct" or "NO adduct" refers to compounds and functional groups which, under physiological conditions, can donate, release and/or directly or indirectly transfer any of the three redox forms of nitrogen monoxide ($NO^+$, $NO^-$, NO.), such that the biological activity of the nitrogen monoxide species is expressed at the intended site of action.

"Nitric oxide releasing" or "nitric oxide donating" refers to methods of donating, releasing and/or directly or indirectly transferring any of the three redox forms of nitrogen monoxide ($NO^+$, $NO^-$, NO.), such that the biological activity of the nitrogen monoxide species is expressed at the intended site of action.

"Alkyl" refers to a lower alkyl group, a haloalkyl group, an alkenyl group, an alkynyl group, a bridged cycloalkyl group, a cycloalkyl group or a heterocyclic ring, as defined herein.

"Lower alkyl" refers to branched or straight chain acyclic alkyl group comprising one to about ten carbon atoms (preferably one to about eight carbon atoms, more preferably one to about six carbon atoms). Exemplary lower alkyl groups include methyl, ethyl, n-propyl, isopropyl, n-butyl, isobutyl, sec-butyl, t-butyl, pentyl, neopentyl, iso-amyl, hexyl, octyl, and the like.

"Haloalkyl" refers to a lower alkyl group, an alkenyl group, an alkynyl group, a bridged cycloalkyl group, a cycloalkyl group or a heterocyclic ring, as defined herein, to which is appended one or more halogens, as defined herein. Exemplary haloalkyl groups include trifluoromethyl, chloromethyl, 2-bromobutyl, 1-bromo-2-chloro-pentyl, and the like.

"Alkenyl" refers to a branched or straight chain $C_2$–$C_{10}$ hydrocarbon (preferably a $C_2$–$C_8$ hydrocarbon, more preferably a $C_2$–$C_6$ hydrocarbon) which can comprise one or more carbon-carbon double bonds. Exemplary alkenyl groups include propylenyl, buten-1-yl, isobutenyl, penten-1-yl, 2,2-methylbuten-1-yl, 3-methylbuten-1-yl, hexan-1-yl, hepten-1-yl, octen-1-yl, and the like.

"Alkynyl" refers to an unsaturated acyclic $C_2$–$C_{10}$ hydrocarbon (preferably a $C_2$–$C_8$ hydrocarbon, more preferably a $C_2$–$C_6$ hydrocarbon) which can comprise one or more carbon-carbon triple bonds. Exemplary alkynyl groups include ethynyl, propynyl, butyn-1-yl, butyn-2-yl, pentyl-1-yl, pentyl-2-yl, 3-methylbutyn-1-yl, hexyl-1-yl, hexyl-2-yl, hexyl-3-yl, 3,3-dimethyl-butyn-1-yl, and the like.

"Bridged cycloalkyl" refers to two or more cycloalkyl groups, heterocyclic groups, or a combination thereof fused via adjacent or non-adjacent atoms. Bridged cycloalkyl groups can be unsubstituted or substituted with one, two or three substituents independently selected from alkyl, alkoxy, amino, alkylamino, dialkylamino, hydroxy, halo, carboxyl, alkylcarboxylic acid, aryl, amidyl, ester, alkylcarboxylic ester, carboxamido, alkylcarboxamido, oxo and nitro. Exemplary bridged cycloalkyl groups include adamantyl, decahydronapthyl, quinuclidyl, 2,6-dioxabicyclo(3.3.0)octane, 7-oxabycyclo(2.2.1)heptyl, 8-azabicyclo(3,2,1)oct-2-enyl and the like.

"Cycloalkyl" refers to a saturated or unsaturated cyclic hydrocarbon comprising from about 3 to about 10 carbon atoms. Cycloalkyl groups can be unsubstituted or substituted with one, two or three substituents independently selected from alkyl, alkoxy, amino, alkylamino, dialkylamino, arylamino, diarylamino, alkylarylamino, aryl, amidyl, ester, hydroxy, halo, carboxyl, alkylcarboxylic acid, alkylcarboxylic ester, carboxamido, alkylcarboxamido, oxo and nitro. Exemplary cycloalkyl groups include cyclopropyl, cyclobutyl, cyclopentyl, cyclohexyl, cyclohexenyl, cyclohepta, 1,3-dienyl, and the like.

"Heterocyclic ring or group" refers to a saturated, unsaturated, cyclic or aromatic or polycyclic hydrocarbon group having about 2 to about 10 carbon atoms (preferably about 4 to about 6 carbon atoms) where 1 to about 4 carbon atoms are replaced by one or more nitrogen, oxygen and/or sulfur atoms. Sulfur may be in the thio, sulfinyl or sulfonyl oxidation state. The heterocyclic ring or group can be fused to an aromatic hydrocarbon group. Heterocyclic groups can be unsubstituted or substituted with one, two or three substituents independently selected from alkyl, alkoxy, amino, alkylamino, dialkylamino, arylamino, diarylamino, alkylarylamino, hydroxy, oxo, thial, halo, carboxyl, carboxylic ester, alkylcarboxylic acid, alkylcarboxylic ester, aryl, arylcarboxylic acid, arylcarboxylic ester, amidyl, ester, carboxamido, alkylcarboxamido, arylcarboxamido, sulfonic acid, sulfonic ester, sulfonamido and nitro. Exemplary heterocyclic groups include pyrrolyl, 3-pyrrolinyl,4,5,6-trihydro-2H-pyranyl, pyridinyl, 1,4-dihydropyridinyl, pyrazolyl, triazolyl, pyrimidinyl, pyridazinyl, oxazolyl, thiazolyl, imidazolyl, indolyl, thiophenyl, furanyl, tetrhydrofuranyl, tetrazolyl, 2-pyrrolinyl, 3-pyrrolinyl, pyrrolindinyl, oxazolindinyl 1,3-dioxolanyl, 2,6-dioxabicyclo(3,3,0)octanyl, 2-imidazonlinyl, imidazolindinyl, 2-pyrazolinyl, pyrazolidinyl, isoxazolyl, isothiazolyl, 1,2,3-oxadiazolyl, 1,2,3-triazolyl, 1,3,4-thiadiazolyl, 2H-pyranyl, 4H-pyranyl, piperidinyl, 1,4-dioxanyl, morpholinyl, 1,4-dithianyl, thiomorpholinyl, pyrazinyl, piperazinyl, 1,3,5-triazinyl, 1,3,5-trithianyl, benzo(b)thiophenyl, benzimidazolyl, quinolinyl, and the like.

"Heterocyclic compounds" refer to mono- and polycyclic compounds comprising at least one aryl or heterocyclic ring.

"Aryl" refers to a monocyclic, bicyclic, carbocyclic or heterocyclic ring system comprising one or two aromatic rings. Exemplary aryl groups include phenyl, pyridyl, napthyl, quinoyl, tetrahydronaphthyl, furanyl, indanyl, indenyl, indoyl, and the like. Aryl groups (including bicylic aryl groups) can be unsubstituted or substituted with one, two or three substituents independently selected from alkyl, alkoxy, amino, alkylamino, dialkylamino, arylamino, diarylamino, alkylarylamino, hydroxy, carboxyl, carboxylic ester, alkylcarboxylic acid, alkylcarboxylic ester, aryl, arylcarboxylic acid, arylcarboxylic ester, alkylcarbonyl, arylcarbonyl, amidyl, ester, carboxamido, alkylcarboxamido, carbomyl, sulfonic acid, sulfonic ester, sulfonamido and nitro. Exemplary substituted aryl groups include tetrafluorophenyl, pentafluorophenyl, sulfonamide, alkylsulfonyl, arylsulfonyl, and the like.

"Alkylaryl" refers to an alkyl group, as defined herein, to which is appended an aryl group, as defined herein. Exemplary alkylaryl groups include benzyl, phenylethyl, hydroxybenzyl, fluorobenzyl, fluorophenylethyl, and the like.

"Arylalkyl" refers to an aryl radical, as defined herein, attached to an alkyl radical, as defined herein.

"Cycloalkylalkyl" refers to a cycloalkyl radical, as defined herein, attached to an alkyl radical, as defined herein.

"Heterocyclicalkyl" refers to a heterocyclic ring radical, as defined herein, attached to an alkyl radical, as defined herein.

"Cycloalkenyl" refers to an unsaturated cyclic hydrocarbon having about 3 to about 10 carbon atoms (preferably about 3 to about 8 carbon atoms, more preferably about 3 to about 6 carbon atoms) comprising one or more carbon-carbon double bonds.

"Arylheterocyclic ring" refers to a bi- or tricyclic ring comprised of an aryl ring, as defined herein, appended via two adjacent carbon atoms of the aryl ring to a heterocyclic ring, as defined herein. Exemplary arylheterocyclic rings include dihydroindole, 1,2,3,4-tetra-hydroquinoline, and the like.

"Alkoxy" refers to $R_{50}O$—, wherein $R_{50}$ is an alkyl group, as defined herein. Exemplary alkoxy groups include methoxy, ethoxy, t-butoxy, cyclopentyloxy, and the like.

"Arylalkoxy or alkoxyaryl" refers to an alkoxy group, as defined herein, to which is appended an aryl group, as defined herein. Exemplary arylalkoxy groups include benzyloxy, phenylethoxy, chlorophenylethoxy, and the like.

"Aryloxy" refers to $R_{55}O$—, wherein $R_{55}$ is an aryl group, as defined herein. Exemplary aryloxy groups include napthyloxy, quinolyloxy, isoquinolizinyloxy, and the like.

"Alkoxyalkyl" refers to an alkoxy group, as defined herein, appended to an alkyl group, as defined herein. Exemplary alkoxyalkyl groups include methoxymethyl, methoxyethyl, isopropoxymethyl, and the like.

"Alkoxyhaloalkyl" refers to an alkoxy group, as defined herein, appended to a haloalkyl group, as defined herein.

Exemplary alkoxyhaloalkyl groups include 4-methoxy-2-chlorobutyl and the like.

"Cycloalkoxy" refers to $R_{54}O—$, wherein $R_{54}$ is a cycloalkyl group or a bridged cycloalkyl group, as defined herein. Exemplary cycloalkoxy groups include cyclopropyloxy, cyclopentyloxy, cyclohexyloxy, and the like.

"Haloalkoxy" refers to a haloalkyl group, as defined herein, to which is appended an alkoxy group, as defined herein. Exemplary haloalkyl groups include 1,1,1-trichloroethoxy, 2-bromobutoxy, and the like.

"Hydroxy" refers to —OH.

"Oxo" refers to =O.

"Oxy" refers to $—O^-R_{77}^+$ wherein $R_{77}$ is an organic or inorganic cation.

"Organic cation" refers to a positively charged organic ion. Exemplary organic cations include alkyl substituted ammonium cations, and the like.

"Inorganic cation" refers to a positively charged metal ion. Exemplary inorganic cations include Group I metal cations such as for example, sodium, potassium, and the like.

"Hydroxyalkyl" refers to a hydroxy group, as defined herein, appended to an alkyl group, as defined herein.

"Amino" refers to —NH$_2$.

"Nitrate" refers to —O—NO$_2$.

"Nitrite" refers to —O—NO.

"Thionitrate" refers to —S—NO$_2$.

"Thionitrite" and "nitrosothiol" refer to —S—NO.

"Nitro" refers to the group —NO$_2$ and "nitrosated" refers to compounds that have been substituted therewith.

"Nitroso" refers to the group —NO and "nitrosylated" refers to compounds that have been substituted therewith.

"Nitrile" and "cyano" refer to —CN.

"Halogen" or "halo" refers to iodine (I), bromine (Br), chlorine (Cl), and/or fluorine (F).

"Alkylamino" refers to $R_{50}NH—$, wherein $R_{50}$ is an alkyl group, as defined herein. Exemplary alkylamino groups include methylamino, ethylamino, butylamino, cyclohexylamino, and the like.

"Arylamino" refers to $R_{55}NH—$, wherein $R_{55}$ is an aryl group, as defined herein.

"Dialkylamino" refers to $R_{50}R_{52}N—$, wherein $R_{50}$ and $R_{52}$ are each independently an alkyl group, as defined herein. Exemplary dialkylamino groups include dimethylamino, diethylamino, methyl propargylamino, and the like.

"Diarylamino" refers to $R_{55}R_{60}N—$, wherein $R_{55}$ and $R_{60}$ are each independently an aryl group, as defined herein.

"Alkylarylamino" refers to $R_{50}R_{55}N—$, wherein $R_{50}$ is an alkyl group, as defined herein, and $R_{55}$ is an aryl group, as defined herein.

"Aminoalkyl" refers to an amino group, an alkylamino group, a dialkylamino group, an arylamino group, a diarylamino group, an alkylarylamino group or a heterocyclic ring, as defined herein, to which is appended an alkyl group, as defined herein.

"Aminoaryl" refers to an amino group, an alkylamino group, a dialkylamino group, an arylamino group, a diarylamino group, an alkylarylamino group or a heterocyclic ring, as defined herein, to which is appended an aryl group, as defined herein.

"Thio" refers to —S—.

"Sulfinyl" refers to —S(O)—.

"Methanthial" refers to —C(S)—.

"Thial" refers to =S.

"Sulfonyl" refers to —S(O)$_2$—.

"Sulfonic acid" refers to —S(O)$_2$OR$_{76}$, wherein $R_{76}$ is a hydrogen, an organic cation or an inorganic cation.

"Alkylsulfonic acid" refers to a sulfonic acid group, as defined herein, appended to an alkyl group, as defined herein.

"Arylsulfonic acid" refers to an sulfonic acid group, as defined herein, appended to an aryl group, as defined herein.

"Sulfonic ester" refers to —S(O)$_2$OR$_{58}$, wherein $R_{58}$ is an alkyl group, an aryl group, an alkylaryl group or an aryl heterocyclic ring, as defined herein.

"Sulfonamido" refers to —S(O)$_2$—N(R$_{51}$)(R$_{57}$), wherein $R_{51}$ and $R_{57}$ are each independently a hydrogen atom, an alkyl group, an aryl group, an alkylaryl group, or an arylheterocyclic ring, as defined herein, or $R_{51}$ and $R_{57}$ taken together are a heterocyclic ring, a cycloalkyl group or a bridged cycloalkyl group, as defined herein.

"Alkylsulfonamido" refers to a sulfonamido group, as defined herein, appended to an alkyl group, as defined herein.

"Arylsulfonamido" refers to a sulfonamido group, as defined herein, appended to an aryl group, as defined herein.

"Alkylthio" refers to $R_{50}S—$, wherein $R_{50}$ is an alkyl group, as defined herein.

"Arylthio" refers to $R_{55}S—$, wherein $R_{55}$ is an aryl group, as defined herein.

"Cycloalkylthio" refers to $R_{54}S—$, wherein $R_{54}$ is a cycloalkyl group or a bridged cycloalkyl group, as defined herein. Exemplary cycloalkylthio groups include cyclopropylthio, cyclopentylthio, cyclohexylthio, and the like.

"Alkylsulfinyl" refers to $R_{50}—S(O)—$, wherein $R_{50}$ is an alkyl group, as defined herein.

"Alkylsulfonyl" refers to $R_{50}—S(O)_2—$, wherein $R_{50}$ is an alkyl group, as defined herein.

"Arylsulfinyl" refers to $R_{55}—S(O)—$, wherein $R_{55}$ is an aryl group, as defined herein.

"Arylsulfonyl" refers to $R_{55}—S(O)_2—$, wherein $R_{55}$ is an aryl group, as defined herein.

"Amidyl" refers to $R_{51}C(O)N(R_{57})—$ wherein $R_{51}$ and $R_{57}$ are each independently a hydrogen atom, an alkyl group, an aryl group, an alkylaryl group, or an arylheterocyclic ring, as defined herein.

"Ester" refers to $R_{51}C(O)O—$ wherein $R_{51}$ is a hydrogen atom, an alkyl group, an aryl group, an alkylaryl group, or an arylheterocyclic ring, as defined herein.

"Carbamoyl" refers to —O—C(O)N(R$_{51}$)(R$_{57}$), wherein $R_{51}$ and $R_{57}$ are each independently a hydrogen atom, an alkyl group, an aryl group, an alkylaryl group or an aryl heterocyclic ring, as defined herein, or $R_{51}$ and $R_{57}$ taken together are a heterocyclic ring, a cycloalkyl group or a bridged cycloalkyl group, as defined herein.

"Carbamate" refers to $R_{51}O—C(O)N—(R_{57})$, wherein $R_{51}$ and $R_{57}$ are each independently a hydrogen atom, an alkyl group, an aryl group, an alkylaryl group or an aryl heterocyclic ring, as defined herein, or $R_{51}$ and $R_{57}$ taken together are a heterocyclic ring, a cycloalkyl group or a bridged cycloalkyl group, as defined herein.

"Carboxyl" refers to —C(O)OR$_{76}$, wherein $R_{76}$ is a hydrogen, an organic cation or an inorganic cation, as defined herein.

"Carbonyl" refers to —C(O)—.

"Alkylcarbonyl" or "alkanoyl" refers to $R_{50}$—C(O)—, wherein $R_{50}$ is an alkyl group, as defined herein.

"Arylcarbonyl" or "aroyl" refers to $R_{55}$—C(O)—, wherein $R_{55}$ is an aryl group, as defined herein.

"Carboxylic ester" refers to —C(O)O$R_{58}$, wherein $R_{58}$ is an alkyl group, an aryl group, an alkylaryl group or an aryl heterocyclic ring, as defined herein.

"Alkylcarboxylic acid" and "alkylcarboxyl" refer to an alkyl group, as defined herein, appended to a carboxyl group, as defined herein.

"Alkylcarboxylic ester" refers to an alkyl group, as defined herein, appended to a carboxylic ester group, as defined herein.

"Arylcarboxylic acid" refers to an aryl group, as defined herein, appended to a carboxyl group, as defined herein.

"Arylcarboxylic ester" and "arylcarboxyl" refer to an aryl group, as defined herein, appended to a carboxylic ester group, as defined herein.

"Carboxamido" refers to —C(O)N($R_{51}$)($R_{57}$), wherein $R_{51}$ and $R_{57}$ are each independently a hydrogen atom, an alkyl group, an aryl group, an alkylaryl group or an arylheterocyclic ring, as defined herein, or $R_{51}$ and $R_{57}$ taken together with the nitrogen to which they are attached form a heterocyclic ring, a cycloalkyl group or a bridged cycloalkyl group, as defined herein.

"Alkylcarboxamido" refers to an alkyl group, as defined herein, appended to a carboxamido group, as defined herein.

"Arylcarboxamido" refers to an aryl group, as defined herein, appended to a carboxamido group, as defined herein.

"Urea" refers to —N($R_{59}$)—C(O)N($R_{51}$)($R_{57}$) wherein $R_{51}$, $R_{57}$, and $R_{59}$ are each independently a hydrogen atom, an alkyl group, an aryl group, an alkylaryl group, or an arylheterocyclic ring, as defined herein, or $R_{51}$ and $R_{57}$ taken together with the nitrogen to which they are attached form a heterocyclic ring, as defined herein.

"Phosphoryl" refers to —P($R_{70}$)($R_{71}$)($R_{72}$), wherein $R_{70}$ is a lone pair of electrons, sulfur or oxygen, and $R_{71}$ and $R_{72}$ are each independently a covalent bond, a hydrogen, a lower alkyl, an alkoxy, an alkylamino, a hydroxy or an aryl, as defined herein.

"Silyl" refers to —Si($R_{73}$)($R_{74}$)($R_{75}$), wherein $R_{73}$, $R_{74}$ and $R_{75}$ are each independently covalent bond, a lower alkyl, an alkoxy, an aryl or an arylalkoxy, as defined herein.

The term "sexual dysfunction" generally includes any sexual dysfunction in a patient, including an animal, preferably a mammal, more preferably a human. The patient can be male or female. Sexual dysfunctions can include, for example, sexual desire disorders, sexual arousal disorders, orgasmic disorders and sexual pain disorders. Female sexual dysfunction refers to any female sexual dysfunction including, for example, sexual desire disorders, sexual arousal dysfunctions, orgasmic dysfunctions, sexual pain disorders, dyspareunia, and vaginismus. The female can be pre-menopausal or menopausal. Sexual dysfunction can be caused, for example, by pregnancy, menopause, cancer, pelvic surgery, chronic medical illness or medications. Male sexual dysfunction refers to any male sexual dysfunctions including, for example, male erectile dysfunction and impotence.

The present invention is directed to methods for measuring vasodilation and changes in blood flow in patients following the administration of a nitric oxide donor and/or vasoactive agent using infrared thermography. The monitoring and diagnosing of diseases and disorders related to vasodilation and changes in blood flow, such as, for example, sexual dysfunctions in patients, including males and females, by administering the nitric oxide donors and/or vasoactive agents are also described herein.

A principal aspect of the present invention relates to measuring the temperature of an area of interest using infrared thermography prior to and/or during and/or following administration of at least one nitric oxide donor and/or at least one vasoactive agent. Any infrared thermographic imaging system known to one skilled in the art can be used in the present invention. For example, THERMACAM® X90 infrared focal plane array (FPA) series, THERMACAM SC 1000 series and THERMACAM SC 3000 are available from Inframetrics, Inc., North Billerica, Mass.; AGEMA series are commercially available from FLIR Systems, Inc., Portland, Oreg.; WO 99/10731 discloses the use of microwave enhanced infrared thermography for the detection, location and identification of objects; and WO 99/60630 discloses the use of infrared thermographic imaging systems to monitor the physiological and molecular thermogenic events in animals, plants, tissues and isolated cells; the disclosures of each of which is incorporated by reference herein in its entirety.

One embodiment of the present invention comprises methods for monitoring and/or measuring the vasodilation and changes in blood flow in vasculature using infrared thermography resulting from the administration of at least one compound that donates, transfers or releases nitric oxide, elevates endogenous levels of endothelium-derived relaxing factor, or EDRF in vivo, stimulates endogenous synthesis of nitric oxide or is a substrate for nitric oxide synthase, and/or otherwise directly or indirectly deliver or transfer nitric oxide to a site of its activity, such as on a cell membrane, in vivo (i.e., nitric oxide donor). For example, the method for monitoring and measuring vasodilation and changes in blood flow may comprise (i) measuring the baseline temperature of an area of interest using infrared thermography, (ii) administering to a patient at least one nitric oxide donor, (iii) measuring the temperature of the area of interest during and/or after administering to a patient the at least one nitric oxide donor using infrared thermography, and (iv) comparing the measurements obtained in steps (i) and (iii), wherein a nitric oxide donor that results in an increase in the temperature between step (i) and step (iii) is a vasodilator and a nitric oxide donor that results in a decrease in the temperature between step (i) and step (iii) is a vasoconstrictor. In another embodiment, a plurality of nitric oxide donors can be tested in the methods of the present invention, and the results of each test can be compared to determine which nitric oxide donor is the most effective, i.e., which nitric oxide donor produces the greatest increase in temperature between step (i) and step (iii). The baseline temperature in step (i) may be a previously obtained measurement; or alternatively a measurement taken after the administration of the compound when a stable baseline temperature measurement is obtained. The nitric oxide donor can optionally be administered with at least one vasoactive agent. Contemplated nitric oxide donors and vasoactive agents include all those known in the art and those described herein. The nitric oxide donors and/or vasoactive agents can be administered separately or in the form of a composition. The compounds and compositions of the present invention can also be administered in combination with other medications used for monitoring diseases or disorders.

As used herein, the term "nitric oxide" encompasses uncharged nitric oxide (NO.) and charged nitrogen monoxide species, preferably charged nitrogen monoxide species, such as nitrosonium ion ($NO^+$) and nitroxyl ion ($NO-$). NO. is a highly reactive short-lived species that is potentially toxic to cells. This is critical because the pharmacological efficacy of NO depends upon the form in which it is delivered. In contrast to the nitric oxide radical (NO.), nitrosonium ($NO^+$) does not react with $O_2$ or $O_2^-$ species, and functionalities capable of transferring and/or releasing $NO^+$ and $NO^-$ are also resistant to decomposition in the presence of many redox metals.

The term "nitric oxide" encompasses uncharged nitric oxide (NO.) and charged nitrogen monoxide species, preferably charged nitrogen monoxide species, such as nitrosonium ion ($NO^+$) and nitroxyl ion ($NO-$). The reactive form of nitric oxide can be provided by gaseous nitric oxide. The nitrogen monoxide releasing, delivering or transferring compounds include any and all such compounds which provide nitrogen monoxide to its intended site of action in a form active for its intended purpose. The term "NO adducts" encompasses any nitrogen monoxide releasing, delivering or transferring compounds, including, for example, S-nitrosothiols, nitrites, nitrates, S-nitrothiols, sydnonimines, 2-hydroxy-2-nitrosohydrazines (NONOates), (E)-alkyl-2-((E)hydroxyimino)-5-nitro-3-hexene amines or amides, nitrosoamines, furoxans as well as substrates for the endogenous enzymes which synthesize nitric oxide. NONOates include, but are not limited to, (Z)-1-{N-methyl-N-(6-(N-methyl-ammoniohexyl)amino)}diazen-1-ium-1,2-diolate ("MAHMA/NO"), (Z)-1-(N-(3-ammoniopropyl)-N-(n-propyl)amino)diazen-1-ium-1,2-diolate ("PAPA/NO"), (Z)-1-{N-(3-aminopropyl)-N-(4-(3-aminopropylammonio) butyl)-amino}diazen-1-ium-1,2-diolate (spermine NONOateor "SPER/NO") and sodium (Z)-1-(N,N-diethylamino)diazenium-1,2-diolate (diethylamine NONOate or "DEA/NO") and derivatives thereof. The "NO adducts" can be mono-nitrosylated, poly-nitrosylated, mono-nitrosated and/or poly-nitrosated or a combination thereof at a variety of naturally susceptible or artificially provided binding sites for biologically active forms of nitrogen monoxide.

One group of NO adducts is the S-nitrosothiols, which are compounds that include at least one —S—NO group. These compounds include S-nitroso-polypeptides (the term "polypeptide" includes proteins and polyamino acids that do not possess an ascertained biological function, and derivatives thereof); S-nitrosylated amino acids (including natural and synthetic amino acids and their stereoisomers and racemic mixtures and derivatives thereof); S-nitrosylated sugars; S-nitrosylated, modified and unmodified, oligonucleotides (preferably of at least 5, and more preferably 5–200 nucleotides); straight or branched, saturated or unsaturated, aliphatic or aromatic, substituted or unsubstituted S-nitrosylated hydrocarbons; and S-nitroso heterocyclic compounds. S-nitrosothiols and methods for preparing them are described in U.S. Pat. Nos. 5,380,758 and 5,703,073; WO 97/27749; WO 98/19672; and Oae etal, *Org. Prep. Proc. Int.*, 15(3):165–198 (1983), the disclosures of each of which are incorporated by reference herein in their entirety.

Another embodiment of the present invention is S-nitroso amino acids where the nitroso group is linked to a sulfur group of a sulfur-containing amino acid or derivative thereof. Such compounds include, for example, S-nitroso-N-acetylcysteine, S-nitroso-captopril, S-nitroso-N-acetylpenicillamine, S-nitroso-homocysteine, S-nitroso-cysteine, S-nitroso-glutathione and S-nitroso-cysteinylglycine. In a preferred embodiment, the S-nitroso amino acid is S-nitrosoglutathione.

Suitable S-nitrosylated proteins include thiol-containing proteins (where the NO group is attached to one or more sulfur groups on an amino acid or amino acid derivative thereof) from various functional classes including enzymes, such as tissue-type plasminogen activator (TPA) and cathepsin B; transport proteins, such as lipoproteins; heme proteins, such as hemoglobin and serum albumin; and biologically protective proteins, such as immunoglobulins, antibodies and cytokines. Such nitrosylated proteins are described in WO 93/09806, the disclosure of which is incorporated by reference herein in its entirety. Examples include polynitrosylated albumin where one or more thiol or other nucleophilic centers in the protein are modified.

Other examples of suitable S-nitrosothiols include:

(i) $HS(C(R_e)(R_f))_m SNO$;

(ii) $ONS(C(R_e)(R_f))_m R_e$; and (iii) $H_2N-CH(CO_2H)-(CH_2)_m-C(O)NH-CH(CH_2SNO)-C(O)NH-CH_2-CO_2H$;

wherein m is an integer from 2 to 20; $R_e$ and $R_f$ are each independently a hydrogen, an alkyl, a cycloalkoxy, a halogen, a hydroxy, an hydroxyalkyl, an alkoxyalkyl, an arylheterocyclic ring, an alkylaryl, a cycloalkylalkyl, a heterocyclicalkyl, an alkoxy, a haloalkoxy, an amino, an alkylamino, a dialkylamino, an arylamino, a diarylamino, an alkylarylamino, an alkoxyhaloalkyl, a haloalkoxy, a sulfonic acid, a sulfonic ester, an alkylsulfonic acid, an arylsulfonic acid, an arylalkoxy, an alkylthio, an arylthio, a cycloalkylthio, a cycloalkenyl, a cyano, an aminoalkyl, an aminoaryl, an aryl, an arylalkyl, an alkylaryl, a carboxamido, a alkylcarboxamido, an arylcarboxamido, an arnidyl, a carboxyl, a carbamoyl, a carbamate, an alkylcarboxylic acid, an arylcarboxylic acid, an alkylcarbonyl, an arylcarbonyl, an ester, a carboxylic ester, an alkylcarboxylic ester, an arylcarboxylic ester, a haloalkoxy, a sulfonamido, an alkylsulfonamido, an arylsulfonamido, a sulfonic ester, a urea, a phosphoryl, a nitro, —T—Q, or —$(C(R_e)(R_f))_k$—T—Q, or $R_e$ and $R_f$ taken together with the carbons to which they are attached form a carbonyl, a methanthial, a heterocyclic ring, a cycloalkyl group or a bridged cycloalkyl group; Q is —NO or —$NO_2$; and T is independently a covalent bond, a carbonyl, an oxygen, —$S(O)_o$— or —$N(R_a)R_i$—, wherein o is an integer from 0 to 2, $R_a$ is a lone pair of electrons, a hydrogen or an alkyl group; $R_i$ is a hydrogen, an alkyl, an aryl, an alkylcarboxylic acid, an aryl carboxylic acid, an alkylcarboxylic ester, an arylcarboxylic ester, an alkylcarboxamido, an arylcarboxamido, an alkylaryl, an alkylsulfinyl, an alkylsulfonyl, an arylsulfinyl, an arylsulfonyl, a sulfonamido, a carboxamido, a carboxylic ester, an amino alkyl, an amino aryl, —$CH_2$—$C(T-Q)(R_e)(R_f)$, or —$(N_2O_2-)^-.M^+$, wherein $M^+$ is an organic or inorganic cation; with the proviso that when $R_i$ is —$CH_2$—$C(T-Q)(R_e)(R_f)$ or —$(N_2O_2-).M^+$; then "—T—Q" can be a hydrogen, an alkyl group, an alkoxyalkyl group, an aminoalkyl group, a hydroxy group or an aryl group.

In cases where $R_e$ and $R_f$ are a heterocyclic ring or $R_e$ and $R_f$ when taken together with the carbon atoms to which they are attached are a heterocyclic ring, then $R_i$ can be a substituent on any disubstituted nitrogen contained within the radical wherein $R_i$ is as defined herein.

Nitrosothiols can be prepared by various methods of synthesis. In general, the thiol precursor is prepared first, then converted to the S-nitrosothiol derivative by nitrosation of the thiol group with $NaNO_2$ under acidic conditions (pH is about 2.5) which yields the S-nitroso derivative. Acids which can be used for this purpose include aqueous sulfuric, acetic and hydrochloric acids. The thiol precursor can also be nitrosylated by reaction with an organic nitrite such as tert-butyl nitrite, or a nitrosonium salt such as nitrosonium tetraflurorborate in an inert solvent.

Another group of NO adducts for use in the present invention, where the NO adduct is a compound that donates, transfers or releases nitric oxide, include compounds comprising at least one ON—O—, ON—N— or ON—C— group. The compounds that include at least one ON—O—, ON—N— or ON—C— group are preferably ON—O—, ON—N— or ON—C-polypeptides (the term "polypeptide" includes proteins and polyamino acids that do not possess an ascertained biological function, and derivatives thereof); ON—O, ON—N— or ON—C-amino acids (including natural and synthetic amino acids and their stereoisomers and racemic mixtures); ON—O—, ON—N— or ON—C-sugars; ON—O—, ON—N— or ON—C— modified or unmodified oligonucleotides (comprising at least 5 nucleotides, preferably 5–200 nucleotides); ON—O—, ON—N— or ON—C— straight or branched, saturated or unsaturated, aliphatic or aromatic, substituted or unsubstituted hydrocarbons; and ON—O—, ON—N— or ON—C-heterocyclic compounds.

Another group of NO adducts for use in the present invention include nitrates that donate, transfer or release nitric oxide, such as compounds comprising at least one $O_2N$—O—, $O_2N$—N—, $O_2N$—S— or $O_2N$—C— group. Preferred among these compounds are $O_2N$—O—, $O_2N$—N—, $O_2N$—S— or $O_2N$—C— polypeptides (the term "polypeptide" includes proteins and also polyamino acids that do not possess an ascertained biological function, and derivatives thereof); $O_2N$—O—, $O_2N$—N—, $O_2N$—S— or $O_2N$—C— amino acids (including natural and synthetic amino acids and their stereoisomers and racemic mixtures); $O_2N$—O—, $O_2N$—N—, $O_2N$—S— or $O_2N$—C-sugars; $O_2N$—O—; $O_2N$—N—, $O_2N$—S— or $O_2N$—C— modified and unmodified oligonucleotides (comprising at least 5 nucleotides, preferably 5–200 nucleotides); $O_2N$—O—, $O_2N$—N—, $O_2N$—S— or $O_2N$—C— straight or branched, saturated or unsaturated, aliphatic or aromatic, substituted or unsubstituted hydrocarbons; and $O_2N$—O—, $O_2N$—N—, $O_2N$—S— or $O_2N$—C— heterocyclic compounds. Preferred examples of compounds comprising at least one $O_2N$—O—, $O_2N$—N—, $O_2N$—S— or $O_2N$—C— group include isosorbide dinitrate, isosorbide mononitrate, clonitrate, erythrityltetranitrate, mannitol hexanitrate, nitroglycerin, pentaerythritoltetranitrate, pentrinitrol and propatylnitrate.

Another group of NO adducts are N-oxo-N-nitrosoamines that donate, transfer or release nitric oxide and are represented by the formula: $R^1R^2$—N(O—$M^+$)—NO, where $R^1$ and $R^2$ are each independently a polypeptide, an amino acid, a sugar, a modified or unmodified oligonucleotide, a straight or branched, saturated or unsaturated, aliphatic or aromatic, substituted or unsubstituted hydrocarbon, or a heterocyclic group, and $M^+$ is as defined herein.

Another group of NO adducts are thionitrates that donate, transfer or release nitric oxide and are represented by the formula: $R^1$—(S)—$NO_2$, where $R^1$ is a polypeptide, an amino acid, a sugar, a modified or unmodified oligonucleotide, a straight or branched, saturated or unsaturated, aliphatic or aromatic, substituted or unsubstituted hydrocarbon, or a heterocyclic group. Preferred are those compounds where $R^1$ is a polypeptide or hydrocarbon with a pair or pairs of thiols that are sufficiently structurally proximate, i.e., vicinal, that the pair of thiols will be reduced to a disulfide. Compounds which form disulfide species release nitroxyl ion (NO–) and uncharged nitric oxide (NO.).

The present invention is also directed to compounds that stimulate endogenous NO or elevate levels of endogenous endothelium-derived relaxing factor (EDRF) in vivo or are substrates for the enzyme, nitric oxide synthase. Such compounds include, for example, L-arginine, L-homoarginine, and N-hydroxy-L-arginine, including their nitrosated and nitrosylated analogs (e.g., nitrosated L-arginine, nitrosylated L-arginine, nitrosated N-hydroxy-L-arginine, nitrosylated N-hydroxy-L-arginine, nitrosated L-homoarginine and nitrosylated L-homoarginine), precursors of L-arginine and/or physiologically acceptable salts thereof, including, for example, citrulline, ornithine, glutamine, lysine, polypeptides comprising at least one of these amino acids, inhibitors of the enzyme arginase (e.g., N-hydroxy-L-arginine and 2(S)-amino-6-boronohexanoic acid) and the substrates for nitric oxide synthase, cytokines, adenosin, bradykinin, calreticulin, bisacodyl, and phenolphthalein. EDRF is a vascular relaxing factor secreted by the endothelium, and has been identified as nitric oxide (NO) or a closely related derivative thereof (Palmer et al, *Nature,* 327:524–526 (1987); Ignarro et al, *Proc. Natl. Acad. Sci. USA,* 84:9265–9269 (1987)).

Another embodiment of the present invention comprises methods for monitoring and/or measuring the vasodilation and changes in blood flow in vasculature using infrared thermography resulting from the administration of at least one vasoactive agent. For example, the method for monitoring and measuring vasodilation and changes in blood flow may comprise (i) measuring the baseline temperature of an area of interest using infrared thermography, (ii) administering to a patient at least one vasoactive agent, (iii) measuring the temperature of the area of interest during and/or after administering the at least one vasoactive agent using infrared thermography, and (iv) comparing the measurements obtained in steps (i) and (iii), wherein a vasoactive agent that results in an increase in the temperature is a vasodilator and a vasoactive that results in a decrease in the temperature is a vasoconstrictor. In another embodiment, a plurality of vasoactive agents may be tested in the methods of the present invention, and the results of each test can be compared to determine which vasoactive agent is the most effective, i.e., which vasoactive agent produces the greatest increase in temperature between step (i) and step (iii). The baseline temperature in step (i) may be a previously obtained measurement; or alternatively a measurement taken after the administration of the compound when a stable baseline temperature measurement is obtained. The vasoactive agent can optionally be administered with a nitric oxide donor. Contemplated vasoactive agents and nitric oxide donors include all those known in the art and those described herein. The nitric oxide donors and/or vasoactive agents can be administered separately or in the form of a composition. The compounds and compositions of the present invention can also be administered in combination with other medications used for monitoring diseases or disorders.

Suitable vasoactive agents that can be used for the methods described herein include, but are not limited to, potassium channel activators (such as, for example, nicorandil, pinacidil, cromakalim, minoxidil, aprilkalim, loprazolam and the like); calcium channel blockers (such as, for example, nifedipine, veraparmil, diltiazem, gallopamil, niludipine, nimodipins, nicardipine, and the like); β-blockers (such as, for example, butixamine, dichloroisoproterenol, propanolol, alprenolol, bunolol, nadolol, oxprenolol, perbutolol, pinodolol, sotalol, timolol, metoprolol, atenolol, acebutolol, bevantolol, pafenolol, tolamodol, and the like); long and short acting α-adrenergic receptor antagonists (such as, for example, phenoxybenzamide, dibenamine, doxazosin, terazosin, phentolamine, tolazoline, prozosin, trimazosin, yohimbine, moxisylyte and the like); prostaglandins (such as, for example, $PGE_1$, $PGA_1$, $PGB_1$, $PGF_1$, $PGF_2$, 19-hydroxy-$PGA_1$, 19-hydroxy-$PGB_1$, $PGE_2$, $PGA_2$, $PGB_2$, prostacyclins, thromboxanes, leukotrienes, 6-keto-$PGE_1$ derivatives and carbacyclin derivatives, and the like); phosphodiesterase inhibitors (such as, for example, papaverine, zaprinast, sildenafil, IC 351); adenosine, ergot alkaloids (such as, for example, ergotamine, ergotamine analogs, including, for example, acetergamine, brazergoline, bromerguride, cianergoline, delorgotrile, disulergine, ergonovine maleate, ergotamine tartrate, etisulergine, lergotrile, lysergide, mesulergine, metergoline, metergotamine, nicergoline, pergolide, propisergide, proterguride, terguride and the like); vasoactive intestinal peptides (such as, for example, peptide histidine isoleucine, peptide histidine methionine, substance P, calcitonin gene-related peptide, neurokinin A, bradykinin, neurokinin B, and the like); dopamine agonists (such as, for example, apomorphine, bromocriptine, testosterone, cocaine, strychnine, and the like); opioid antagonists (such as, for example, naltrexone, and the like); endothelin antagonists (such as, for example, bosentan, sulfonamide endothelin antagonists, BQ-123, SQ 28608, and the like); thromboxane inhibitors (such as, for example, SQ 29548, BAY u3405, GR 32191, YM 158, and the like), and mixtures thereof. Suitable vasoactive agents are described more fully in the literature, such as in Goodman and Gilman, The Pharmacological Basis of Therapeutics (9th Edition), McGraw-Hill, 1995; and the Merck Index on CD-ROM, Twelfth Edition, Version 12:1, 1996; and on STN Express, file phar and file registry.

Another embodiment of the present invention comprises methods for monitoring and measuring sexual dysfunctions and/or sexual arousal in patients, preferably males and females, most preferably females, using infrared thermography resulting from the administration of at least one nitric oxide donor and/or at least one vasoactive agent. For example, the method for monitoring and measuring female sexual dysfunction may comprise (i) measuring the baseline temperature of the gentialia using infrared thermography, (ii) administering to a patient at least one nitric oxide donor and/or at least one vasoactive agent, (iii) measuring the temperature of the gentialia during and/or after administering to a patient the nitric oxide donor and/or the vasoactive agent using infrared thermography, and (iv) comparing the measurements obtained in steps (i) and (iii), wherein a compound that results in an increase in the temperature between step (i) and step (iii) is a sexual enhancer and a compound that results in a decrease in the temperature between step (i) and step (iii) is a sexual inhibitor. The baseline temperature in step (i) may be a previously obtained measurement; or alternatively a measurement taken after the administration of the compound when a stable baseline temperature measurement is obtained. Contemplated nitric oxide donors and vasoactive agents include all those known in the art and those described herein. The nitric oxide donors and/or vasoactive agents can be administered separately or in the form of a composition. The compounds and compositions of the present invention can also be administered in combination with other medications used for monitoring diseases or disorders.

Yet another embodiment of present invention comprises methods for monitoring and diagnosing diseases and disorders resulting from vasodilation and changes in blood flow using infrared thermography. The diseases and disorders resulting from changes in vasodilation and blood flow include, or example, Raynaud's syndrome, inflammation, hypertension, gastrointestinal disorders and central nervous system disorders. For example, the method for monitoring and diagnosing diseases and disorders resulting from vasodilation and changes in blood flow may comprise (i) measuring the baseline temperature of an area of interest using infrared thermography, (ii) administering to a patient at least one nitric oxide donor and/or at least one vasoactive agent, (iii) measuring the temperature of the area of interest during and/or after administering to a patient the at least one nitric oxide donor and/or at least one vasoactive agent using infrared thermography, and (iv) comparing the measurements obtained in steps (i) and (iii), wherein a compound that results in an increase in the temperature between step (i) and step (iii) will be useful for treating the diseases and disorders described herein. The baseline temperature in step (i) may be a previously obtained measurement; or alternatively a measurement taken any time after the administration of the at least one nitric oxide donor and/or at least one vasoactive agent when a stable baseline temperature measurement is obtained. Contemplated nitric oxide donors and vasoactive agents include all those known in the art and those described herein. The nitric oxide donors and/or vasoactive agents can be administered separately or in the form of a composition. The compounds and compositions of the present invention can also be administered in combination with other medications used for monitoring diseases or disorders.

Yet another embodiment of present invention comprises methods for identifying, characterizing, ranking and selecting compounds for the treatment of a disease and disorder resulting from vasodilation and changes in blood flow using infrared thermography. For example, the method for identifying, characterizing, ranking and selecting compounds for the treatment of a disease and disorder resulting from vasodilation and changes in blood flow may comprise (i) measuring the baseline temperature of an area of interest using infrared thermography, (ii) administering to a patient a test compound, (iii) measuring the temperature of the area of interest during and/or after administering to a patient the test compound using infrared thermography, and (iv) comparing the measurements obtained in steps (i) and (iii), wherein a compound that results in an increase in the temperature between step (i) and step (iii) is effective for the treatment of the disease or disorder and a compound that produces no temperature change or results in a decrease in the temperature between step (i) and step (iii) is not effective for the treatment of the disease or disorder. The greater the increase in temperature of the area of interest between step (i) and step (iii) the more potent the compound. In another embodiment, a plurality of test compounds can be tested in the methods of the present invention, and the results from each test can be compared to determine which test compound is the most effective, i.e., which test compound produces the greatest increase in temperature between step (i) and step (iii). In some instances it may be desirable to use the methods of the present invention to find compounds which produce the greatest decrease in temperature between step (i) and step (ii), or which do not produce any change in temperature between step (i) and step (iii). The baseline temperature in step (i) may be a previously obtained measurement; or alternatively a measurement taken any time after the administration of the test compound when a stable baseline temperature measurement is obtained.

Yet another embodiment of the present invention provides compositions comprising at least one S-nitrosothiol compound and at least one penetration enhancers that may be used to diagnose, monitor and/or treat female sexual dysfunctions. The S-nitrosothiol compound may preferably be S-nitrosoglutathione. The penetration enhancer, may preferably be a glyceride, such as, MIGLYOL®, and/or a polyglcolyzed glyceride, such as, LABROSOL® and/or LABROFIL®, or mixtures thereof. These compositions may further comprise at least one vasoactive agent and/or at least one nitric oxide donor, or mixtures thereof.

In a particular embodiment, the glyceride penetration enhancer MIGLYOL® is MIGLYLOL® 812N obtained from Condea Vista Company, Houston, Tex. MIGLYOL® 812N is a mixture of caprylic triglycerides and capric triglycerides. It can also contain decanoly triglycerides, octanoyl triglycerides and $C_8$–$C_{12}$ triglycerides.

The polyglycolyzed glyceride may be saturated or unsaturated and may include ethoxylated glycerides and polyethylene glycol esters. In a particular embodiment, the saturated polyglycolyzed glyceride is a glyceryl caprylate/caprate and PEG-8 (polyethylene glycol) caprylate/caprate complex known as LABRASOL® (Gattefosse Corp., New York). Suitable unsaturated polyglycolyzed glycerides are apricot kernel oil PEG-6 complex (LABRAFIL® M-1944 CS), almond oil PEG-6 complex (LABRAFIL® M-1966 CS), peanut oil PEG-6 complex (LABRAFIL® M-1969 CS), olive oil PEG-6 complex (LABRAFIL® M-1980 CS) and corn oil PEG-6 complex (LABRAFIL® M-2125 CS), all available from Gattefosse Corp., New York. Suitable ethoxylated glyceride, include, but are not limited to, $C_8$–$C_{10}$ carbon chain, for example glyceryl caprylate/caprate PEG-4 complex.

When administered in vivo, the nitric oxide donors and/or vasoactive agents of the present invention may be administered with pharmaceutically acceptable carriers and in dosages described herein. When the nitric oxide donors and/or vasoactive agents of the present invention are administered as a mixture of at least one nitric oxide donor and at least one vasoactive agent, they can also be used in combination with one or more additional compounds (e.g., therapeutic agents used to treat, diagnose and monitor the disease and disorder). When administered separately, the nitric oxide donor(s) and/or vasoactive agent can be administered simultaneously with, subsequently to, or prior to administration of the other additional compound(s) to treat or monitor the diseases described herein.

The compounds and compositions of the present invention can be administered by any available and effective delivery system including, but not limited to, orally, bucally, parenterally, by inhalation spray (oral or nasal), by topical application, by injection into the corpus cavernosum tissue, by transurethral drug delivery, vaginally, or rectally (e.g., by the use of suppositories) in dosage unit formulations containing conventional nontoxic pharmaceutically acceptable carriers, adjuvants, and vehicles, as desired. Parenteral includes subcutaneous injections, intravenous injections, intramuscular injections, intrasternal injections, and infusion techniques. Parenteral also includes injection into the corpus cavernosum tissue, which can be conducted using any effective injection system including, but not limited to, conventional syringe-and-needle systems or needleless injection devices.

Solid dosage forms for oral administration can include capsules, tablets, effervescent tablets, chewable tablets, pills, powders, effervescent powders, sachets, granules and gels. In such solid dosage forms, the active compounds can be admixed with at least one inert diluent such as sucrose, lactose or starch. Such dosage forms can also comprise, as in normal practice, additional substances other than inert diluents, e.g., lubricating agents such as magnesium stearate. In the case of capsules, tablets, effervescent tablets, and pills, the dosage forms can also comprise buffering agents. Soft gelatin capsules can be prepared to contain a mixture of the active compounds or compositions of the present invention and vegetable oil. Hard gelatin capsules can contain granules of the active compound in combination with a solid, pulverulent carrier such as lactose, saccharose, sorbitol, mannitol, potato starch, corn starch, amylopectin, cellulose derivatives of gelatin. Tablets and pills can be prepared with enteric coatings.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

Suppositories for vaginal or rectal administration of the compounds and compositions of the invention can be prepared by mixing the compounds or compositions with a suitable nonirritating excipient such as cocoa butter and polyethylene glycols which are solid at room temperature but liquid at body temperature, such that they will melt and release the drug.

Injectable preparations, for example, sterile injectable aqueous or oleaginous suspensions can be formulated according to the known art using suitable dispersing agents, wetting agents and/or suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be used are water, Ringer's solution, and isotonic sodium chloride solution. Sterile fixed oils are also conventionally used as a solvent or suspending medium.

Topical administration, which is well known to one skilled in the art, involves the delivery of pharmaceutical agents via percutaneous passage of the drug into the systemic circulation of the patient. Topical administration includes vaginal administration, vulval administration, penile administration and rectal administration. Topical administration can also involve transdermal patches or iontophoresis devices. Other components can be incorporated into the transdermal patches as well. For example, compositions and/or transdermal patches can be formulated with one or more preservatives or bacteriostatic agents including, but not limited to, methyl hydroxybenzoate, propyl hydroxybenzoate, chlorocresol, benzalkonium chloride, and the like.

Dosage forms for topical administration of the compounds and compositions of the present invention preferably include creams, sprays, lotions, gels, ointments, emulsions, coatings for condoms, liposomes, foams, and the like. Administration of the cream, spray, ointment, lotion, gel, emulsion, coating, liposome, or foam can be accompanied by the use of an applicator or by transurethral drug delivery using a syringe with or without a needle or penile insert or device, or by clitoral, vulval or vaginal delivery, and is within the skill of the art. Alternatively, the compositions may be contained within a vaginal ring, tampon, suppository, sponge, pillow, puff, or osmotic pump system;

these platforms are useful solely for vaginal delivery. Typically a lubricant and/or a local anesthetic for desensitization can also be included in the formulation or provided for use as needed. Lubricants include, for example, K-Y jelly (available from Johnson & Johnson) or a lidocaine jelly, such as XYLOCAINE® 2% jelly (available from Astra Pharmaceutical Products). Local anesthetics include, for example, novocaine, procaine, tetracaine, benzocaine and the like.

Ointments are semisolid preparations that are typically based on petrolatum or other petroleum derivatives. The specific ointment base to be used, as will be appreciated by those skilled in the art, is one that will provide for optimum drug delivery. An ointment base should be inert, stable, nonirritating and nonsensitizing. Ointment bases may be grouped in four classes: oleaginous bases; emulsifiable bases; emulsion bases; and water-soluble bases. Oleaginous ointment bases include, for example, vegetable oils, fats obtained from animals, semisolid hydrocarbons obtained from petroleum, and the like. Emulsifiable ointment bases, also known as absorbent ointment bases, contain little or no welter and include, for example, hydroxystearin sulfate, anhydrous lanolin, hydrophilic petrolatum, and the like. Emulsion ointment bases are either water-in-oil (W/O) emulsions or oil-in-water (O/W) emulsions, and include, for example, cetyl alcohol, glyceryl monostearate, lanolin and stearic acid, and the like. In a particular embodiment, water-soluble ointment bases are preferred and are prepared from polyethylene glycols of varying molecular weight, and can be determined by standard techniques as described in Remington: The Science and Practice of Pharmacy.

Lotions are preparations that may be applied without friction, and are typically liquid or semiliquid preparations in which solid particles, including the active agent, are present in a water or alcohol base. Lotions are usually suspensions of solids, and in a particular embodiment, may comprise a liquid oily emulsion of the oil-in-water type. It is generally necessary that the insoluble matter in a lotion be finely divided. Lotions will typically contain suspending agents to produce better dispersions as well as compounds useful for localizing the active agent in contact with the skin, such as, for example, methylcellulose, sodium carboxymethyl-cellulose, and the like.

Emulsion formulations are generally formed from a dispersed phase (for example., a pharmacologically active agent), a dispersion medium and an emulsifing agent. If desired, emulsion stabilizers can be included in the formulation as well. A number of pharmaceutically useful emulsions are known in the art, including, for example, oil-in-water (o/w) formulations, water-in-oil (w/o) formulations and multiple emulsions such as w/o/w or o/w/o formulations. Emulsifying agents suitable for use in such formulations include, but are not limited to, TWEEN 60®, SPAN 80®, cetostearyl alcohol, myristyl alcohol, glyceryl monostearate, sodium lauryl sulfate, and the like.

Creams are, as known in the art, viscous liquid or semisolid emulsions, either oil-in-water or water-in-oil. Cream bases are water-washable, and contain an oil phase, an emulsifier and an aqueous phase. The oil phase, also sometimes called the "internal" phase, is generally comprised of petrolatum and a fatty alcohol such as, cetyl alcohol, stearyl alcohol, and the like; the aqueous phase usually, although not necessarily, exceeds the oil phase in volume, and generally contains a humectant. The emulsifier in a cream formulation is generally a nonionic, anionic, cationic or amphoteric surfactant.

The ointments, lotions, emulsions and creams are formed by dispersing finely divided or dissolved the nitric oxide donor(s) and/or vasoactive agent(s) uniformly throughout the vehicle or base using conventional techniques, typically by levigating the compound with a small quantity of the base to form a concentrate which is then diluted geometrically with further base. Alternatively, a mechanical mixer may be used. Creams, lotions and emulsions are formed by way of a two-phase heat system, wherein oil-phase ingredients are combined under heat to provide a liquified, uniform system. The aqueous-phase ingredients are separately combined using heat. The oil and aqueous phases are then added together with constant agitation and allowed to cool. At this point, concentrated agents may be added as a slurry. Volatile or aromatic materials can be added after the emulsion has sufficiently cooled. Preparation of such pharmaceutical compositions is within the general skill of the art. See, e.g., Remington's Pharmaceutical Sciences, 18th Ed. (Easton, Pa.: Mack Publishing Company, 1990).

The vasoactive agents can also be incorporated into gel formulations using known techniques. Two-phase gel systems generally comprise a suspension or network of small, discrete particles interpenetrated by a liquid to provide a dispersed phase and a liquid phase. Single-phase gel systems are formed by distributing organic macromolecules uniformly throughout a liquid such that there are no apparent boundaries between the dispersed and liquid phases. Suitable gelling agents for use herein include synthetic macromolecules, such as, CARBOMERS®, polyvinyl alcohols, and polyoxyethylene-polyoxypropylene copolymers, and the like; gums such as, tragacanth, as well as sodium alginate, gelatin, methylcellulose, sodium carboxymethylcellulose, methylhydroxyethyl cellulose, hydroxyethyl cellulose, and the like. In order to prepare a uniform gel, dispersing agents such as alcohol or glycerin may be added, or the gelling agent may be dispersed by trituration, mechanical mixing or stirring, or combinations thereof.

The compounds and compositions of the present invention will typically be administered in a pharmaceutical composition containing one or more carriers or excipients, i.e., pharmaceutically acceptable organic or inorganic carrier substances suitable for parenteral application which do not deleteriously react with the active compounds. Examples of pharmaceutically acceptable carriers include, for example, water, salt solutions, alcohol, silicone, waxes, petroleum jelly, vegetable oils, polyethylene glycols, propylene glycol, liposomes, sugars, gelatin, lactose, amylose, magnesium stearate, talc, surfactants, silicic acid, viscous paraffin, perfume oil, fatty acid monoglycerides and diglycerides, petroethral fatty acid esters, hydroxymethyl-cellulose, polyvinylpyrrolidone, and the like.

The pharmaceutical preparations can be sterilized and if desired, mixed with auxiliary agents which do not deleteriously react with the active compounds, e.g., lubricants, preservatives, stabilizers, wetting agents, emulsifiers, salts for influencing osmotic pressure, buffers, colorings, flavoring and/or aromatic substances, and the like. For parenteral application, particularly suitable vehicles consist of solutions, preferably oily or aqueous solutions, as well as suspensions, emulsions, or implants. Aqueous suspensions may contain substances which increase the viscosity of the suspension and include, for example, sodium carboxymethyl cellulose, sorbitol and/or dextran. Optionally, the suspension may also contain stabilizers.

The pharmaceutical compositions may also include a detergent in the formulation, in an amount effective to increase solubility of the nitric oxide donor and/or vasoactive agent in the vehicle and bioavailability of the agent following administration. The detergent will typically be a nonionic, anionic, cationic or amphoteric surfactant. The surfactant is selected such that local irritation at the site of administration is avoided. Surfactants include, for example, TERGITOL.® and TRITON® surfactants (Union Carbide Chemicals and Plastics, Danbury, Conn. polyoxyethylene sorbitan fatty acid esters, e.g., TWEEN® surfactants (Atlas Chemical Industries, Wilmington, Del.), such as, for example, polyoxyethylene 20 sorbitan monolaurate (TWEEN® 20), polyoxyethylene (4) sorbitan monolaurate (TWEEN® 21), polyoxyethylene 20 sorbitan monopalmitate (TWEEN® 40), polyoxyethylene 20 sorbitan monooleate (TWEEN® 80, and the like; polyoxyethylene 4 lauryl ether (BRIJ® 30), polyoxyethylene 23 lauryl ether (BRIJ 35), polyoxyethylene 10 oleyl ether (BRIJ® 97); polyoxyethylene glycol esters, such as, for example, poloxyethylene 8 stearate (MYRJ® 45), poloxyethylene 40 stearate (MYRJ® 52) polyoxyethylene alkyl ethers, and the like; or mixtures thereof.

The pharmaceutical preparation may also include one or more permeation enhancers. Permeation enhancers include those generally useful in conjunction with topical, transdermal or transmucosal drug delivery. Permeation enhancers include, for example, dimethylsulfoxide (DMSO), dimethyl formamide (DMF), N,N-dimethylacetamide (DMA), decylmethylsulfoxide ($C_{10}$ MSO), polyethylene glycol monolaurate (PEGML), polyethyleneglycol, glycerol monolaurate, lecithin, the 1-substituted azacycloheptan-2-ones, such as, 1-n-dodecylcyclazacycloheptan-2-one (available under the trademark AZONE® from Nelson Research & Development Co., Irvine, Calif.), lower alkanols (e.g., ethanol), $C_6$ to $C_{20}$-hydrocarbyl substituted 1,3-dioxane, $C_6$ to $C_{20}$-hydrocarbyl substituted 1,3-dioxolane and $C_6$ to $C_{20}$-hydrocarbyl substituted acetal, such as, SEPA® (available from Macrochem Co., Lexington, Mass.), alkonates, such as, alkyl-2-(N,N-disubstituted amino)-alkonate ester, N,N-disubstituted amino)-alkanol alkanoate, and the like, glycerides, such as mono, di and triglycerides and mixtures thereof, such as for example MIGLYOL® (Condea Vista Company, Houston, Tex.) and the like; polyglycolyzed glycerides, such as, for example, LABRASOL® and LABRAFIL®, and the like; and surfactants as discussed above, including, for example, TERGITOL.® and TRITON® surfactants, NONOXYNOL-9® and TWEEN-80®. In particular embodiments the penetration enhancers may be MIGLYOL®, LABRASOL® or LABRAFIL®, including mixtures thereof.

In some cases, the formulations may include one or more compounds effective to inhibit enzymes present in the vaginal or vulvar areas which could degrade or metabolize the pharmacologically active agent. For example, with a prostaglandin as the vasoactive agent, it may be preferred to include an effective inhibiting amount of a compound effective to inhibit prostaglandin-degrading enzymes. Such compounds include, for example, fatty acids, fatty acid esters, and NAD inhibitors.

Various delivery systems are known and can be used to administer the compounds or compositions of the present invention, including, for example, encapsulation in liposomes, microbubbles, emulsions, microparticles, microcapsules and the like. The required dosage can be administered as a single unit or in a sustained release form.

The bioavailabilty of the compositions can be enhanced by micronization of the formulations using conventional techniques such as grinding, milling, spray drying and the like in the presence of suitable excipients or agents such as phospholipids or surfactants. The bioavailability and absorption of the nitric oxide donor and/or vasoactive agent can be increased by the addition of tabletting excipients, such as, for example β-cyclodextrin, a β-cyclodextrin derivative, such as for example, hydroxypropyl-β-cyclodextrin (HPBCD), and the like. Inclusion complexes are complexes formed by interaction of macrocyclic compounds containing an intramolecular cavity of molecular dimensions with the smaller, pharmacologically active agent. Preferred inclusion complexes are formed from α-, β- and γ-cyclodextrins, or from clathrates, in which the "host" molecules form a crystal lattice containing spaces in which "guest" molecules (i.e., in this case, the nitric oxide donor and/or vasoactive agent) will fit. See, e.g., Hagan, Clathrate Inclusion Compounds (New York: Reinhold, 1962).

Liposomes are microscopic vesicles having a lipid wall comprising a lipid bilayer, and can be used as drug delivery systems as well. Generally, liposome formulations are preferred for poorly soluble or insoluble pharmaceutical agents. Liposomal preparations for use in the pressent invention include cationic (positively charged), anionic (negatively charged) and neutral preparations. Cationic liposomes are readily available. For example, N(1-2,3-dioleyloxy)propyl)-N,N,N-triethylammonium (DOTMA) liposomes are available under the tradename LIPOFECTIN® (GIBCO BRL, Grand Island, N.Y.). Similarly, anionic and neutral liposomes are readily available as well, from Avanti Polar Lipids (Birmingham, Ala.), or can be easily prepared using readily available materials. Such materials include phosphatidyl choline, cholesterol, phosphatidyl ethanolamine, dioleoylphosphatidyl choline (DOPC), dioleoylphosphatidyl glycerol (DOPG), dioleoylphoshatidyl ethanolamine (DOPE), and the like. These materials can also be mixed with DOTMA in appropriate ratios. Methods for making liposomes using these materials are well known in the art. See Remington's Pharmaceutical Sciences, supra.

The release of the nitric oxide donor and/or vasoactive agent can be controlled by dissolution (bioerosion) of a polymer using either encapsulated dissolution control or matrix dissolution control. In encapsulated dissolution control, the vasoactive agent is coated with a membrane of slowly dissolving polymeric or wax materials. When the encapsulating membrane has dissolved, the agent core is available for immediate release and adsorption across the epithelial or mucosal surfaces of the vagina or vulvar area. Bioerodible coating materials may be selected from a variety of natural and synthetic polymers, depending on the agent to be coated and the desired release characteristics. Exemplary coating materials include gelatins, carnauba wax, shellacs, ethylcellulose, cellulose acetate phthalate, cellulose acetate butyrate, and the like. Release of the compound is controlled by adjusting the thickness and dissolution rate of the polymeric membrane. A uniform sustained release can be attained by compressing a population of particles of the agent with varying membrane thickness (e.g., varying erosion times) into a tablet form for a single administration.

In matrix dissolution control, the nitric oxide donor and/or vasoactive agent is dissolved or dispersed within a matrix of, such as, for example, an erodible wax. The compound is released for adsorption across the epithelial or mucosal surfaces of the vagina or vulvar area as the matrix bioerodes. The rate of compound availability is generally controlled by the rate of penetration of the dissolution media (i.e., vaginal fluids) into the matrix, wherein the rate of penetration is dependent on the porosity of the matrix material. Bioerodible matrix dissolution delivery systems can be prepared by compressing the nitric oxide donor and/or vasoactive agent with a slowly soluble polymer carrier into a tablet or suppository form. There are several methods of preparing drug/wax particles including congealing and aqueous dispersion techniques. In congealing methods, the vasodilating agent is combined with a wax material and either spray-congealed, or congealed and then screened. For an aqueous dispersion, the vasodilating agent/wax combination is sprayed or placed in water and the resulting particles collected. Matrix dosage formulations can be formed by compaction or compression of a mixture of vasodilating agent, polymer and excipients.

In an alternative embodiment, the compositions of the present invention may be administered as biodegradable adhesive film or sheet which adhere to the vulvar area. Such drug delivery systems are generally composed of a biodegradable adhesive polymer based on a polyurethane, a poly(lactic acid), a poly(glycolic acid), a poly(ortho ester), a polyanhydride, a polyphosphazene, or a mixture or copolymer thereof. Preferred biodegradable adhesive polymers include, for example, polyurethanes and block copolyurethanes containing peptide linkages, simple mixtures of polyurethanes and polylactides, and copolymers of acrylates and mono- or disaccharide residues.

The compounds and compositions of the present invention can be formulated as pharmaceutically acceptable salts. Pharmaceutically acceptable salts include, for example, alkali metal salts and addition salts of free acids or free bases. The nature of the salt is not critical, provided that it is pharmaceutically acceptable. Suitable pharmaceutically acceptable acid addition salts may be prepared from an inorganic acid or from an organic acid. Examples of such inorganic acids include, but are not limited to, hydrochloric, hydrobromic, hydroiodic, nitric (nitrate salt), nitrous (nitrite salt), carbonic, sulfuric and phosphoric acid and the like. Appropriate organic acids include, but are not limited to, aliphatic, cycloaliphatic, aromatic, heterocyclic, carboxylic and sulfonic classes of organic acids, such as, for example, formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesuifonic, sulfanilic, stearic, algenic, β-hydroxybutyric, cyclohexylaminosulfonic, galactaric and galacturonic acid and the like. Suitable pharmaceutically acceptable base addition salts include, but are not limited to, metallic salts made from aluminum, calcium, lithium, magnesium, potassium, sodium and zinc or organic salts made from primary, secondary and tertiary amines, cyclic amines, N,N'-dibenzylethylenediamine, chloroprocaine, choline, diethanolamine, ethylenediamine, meglumine (N-methylglucamine) and procaine and the like. All of these salts may be prepared by conventional means from the corresponding compound by reacting, for example, the appropriate acid or base with the compound.

"Therapeutically effective amount" refers to the amount of the nitric oxide donor and/or vasoactive agent which is effective to achieve its intended purpose. In preferred embodiments of the methods described herein, the nitric oxide donor and/or vasoactive agents are administered in a therapeutically effective amount. While individual patient needs may vary, determination of optimal ranges for effective amounts of each nitric oxide donor is within the skill of the art. Generally the dosage regimen for monitoring and idagnosing a condition with the compounds and/or compositions of this invention is selected in accordance with a variety of factors, including the type, age, weight, sex, diet and medical condition of the patient, the severity of the dysfunction, the route of administration, pharmacological considerations such as the activity, efficacy, pharmacokinetic and toxicology profiles of the particular compound used, whether a drug delivery system is used, and whether the compound is administered as part of a drug combination and can be adjusted by one skilled in the art. Thus, the dosage regimen actually employed may vary from the preferred dosage regimen set forth herein.

The amount of a given nitric oxide donor and/or vasoactive agent which will be effective in monitoring and diagnosing a particular dysfunction or condition will depend on the nature of the dysfunction or condition, and can be determined by standard clinical techniques, including reference to Goodman and Gilman, supra; The Physician's Desk Reference, supra; Medical Economics Company, Inc., Oradell, N.J., 1995; and Drug Facts and Comparisons, Inc., St. Louis, Mo., 1993. The precise dose to be used in the formulation will also depend on the route of administration, and the seriousness of the dysfunction or disorder, and should be decided by the physician and the patient's circumstances. Effective doses may be extrapolated from dose-response curves derived from in vitro or animal model test systems and are in the same ranges or less than as described for the commercially available compounds in the Physician's Desk Reference, supra.

In particular embodiments the methods of administration of the nitric oxide donors and/or vasoactive agents for monitoring, diagnosing and treating male sexual dysfunction are by oral administration, by topical application, by injection into the corpus cavernosum, by transurethral administration or by the use of suppositories. The preferred methods of administration for monitoring, diagnosing and treating female sexual dysfunction are by oral administration, topical application or by the use of suppositories. The most preferred mode of administration for female sexual dysfunction is topical application, preferably as an ointment, a cream, a gel, an emulsion, a spray or a lotion. These compositions may contain at least one penetration enhancer to increase the premeability of the nitric oxide donor and/or vasoactive agent across the membrane.

The doses of nitric oxide donors for monitoring and diagnosing sexual dysfunction in the pharmaceutical composition can be in amounts of about 0.001 mg to about 30 g and the actual amount administered will be dependent on the specific nitric oxide donor compound. For example, when L-arginine is the nitric oxide donor, L-arginine can be administered orally in an amount of about 0.25 grams to about 10 grams (equivalent to about 0.5 grams to about 20 grams of L-arginine glutamate), preferably about 2 grams to about 4 grams (equivalent to about 4 grams to about 8 grams of L-arginine glutamate); more preferably about 2.5 grams to about 3.5 grams (equivalent to about 5 grams to about 7 grams of L-arginine glutamate); most preferably about 3 grams (equivalent to 6 grams of L-arginine glutamate).

The α-antagonist, such as phentolamine, can be administered in amounts of about 3.7 mg to about 90 mg (equivalent to about 5 mg to about 120 mg phentolamine mesylate), preferably about 22 mg to about 37 mg (equivalent to about 30 mg to about 50 mg phentolamine mesylate), more preferably about 26 mg to about 34 mg (equivalent to about 35 mg to about 45 mg phentolamine mesylate), even more preferably about 28 mg to about 31 mg (equivalent to about 38 mg to about 42 mg phentolamine mesylate), most preferably about 30 mg (equivalent to about 40 mg phentolamine mesylate).

The α-antagonist, such as yohimbine, can be administered in an amount of about 1.0 mg to about 18.0 mg (equivalent to about 1.1 mg to about 19.8 mg yohimbine hydrochloride), preferably about 4.5 mg to about 6.4 mg, (equivalent to about 5.0 mg to about 7.0 mg yohimbine hydrochloride), more preferably about 5.0 mg to about 6.0 mg, (equivalent to about 5.5 mg to about 6.5 mg yohimbine hydrochloride), most preferably about 5.5 mg (equivalent to about 6.0 mg yohimbine hydrochloride). The yohimbine can also be administered in the form of its pharmaceutical salt, yohimbine tartarate, or yohimbe bark powder or extract that has been standardized to deliver up to about 18 mg of yohimbine.

The present invention also provides pharmaceutical kits comprising one or more containers filled with one or more of the ingredients of the pharmaceutical compounds and/or compositions of the present invention, including, one or more NO donors, and one or more vasoactive agents. Such kits can also include, for example, other compounds and/or compositions (e.g., permeation enhancers, lubricants, and the like), a device(s) for administering the compounds and/or compositions, and written instructions in a form prescribed by a governmental agency regulating the manufacture, use or sale of pharmaceuticals or biological products, which instructions can also reflects approval by the agency of manufacture, use or sale for human administration.

EXAMPLES

The following non-limiting examples are for purposes of illustration only and are not intended to limit the scope of the invention or claims.

Example 1

4-Aza-4-(2-methyl-2-(nitrosothio)propyl)tricyclo (5.2.1.0<2,6>)dec-8-ene-3,5-dione 1a. 4-Aza-4-(2-methyl-2-sulfanylpropyl)tricyclo(5.2.1.0<2,6>)dec-8-ene-3,5-dione A suspension of 1-amino-2-methylpropane-2-thiol hydrochloride (6.72 g, 47.4 mmol) in ethyl acetate (200 mL) was shaken with potassium hydroxide solution (16 M, 3.6 mL, 57.0 mmol). The ethyl acetate solution was separated, dried with sodium sulfate, filtered, and concentrated to give 1-amino-2-methylpropane-2-thiol (2.70 g, 25.7 mmol, 54%). The thiol was dissolved in acetic acid (25 mL) and cis-5-norbomene-endo-2,3-dicarboxylic anhydride (4.17 g, 25.4 mmol) was added. The reaction was stirred at 100° C. for 1 hour and allowed to stand at room temperature over the weekend. The crystals which formed were collected by filtration, washed with acetic acid (4 mL) and a small volume of methanol, and then dried in vacuo to give the title compound (2.22 g, 35%). The filtrate was concentrated, treated with toluene and concentrated (repeat four times). The residue dissolved in dichloromethane and filtered through silica gel to give additional product (2.47 g) contaminated with a little cis-5-norbornene-endo-2,3-dicarboxylic anhydride. $^1$H NMR (CDCl$_3$) δ6.16 (s, 2H), 3.52 (s, 2H), 3.42 (s, 2H), 3.32 (s, 2H), 1.86 (s, 1H), 1.76 (d, J=8.77 Hz, 1H), 1.57 (d, J=8.77 Hz, 1H), 1.30 (s, 6H). $^{13}$C NMR (CDCl$_3$) δ177.9, 134.8, 52.5, 51.0, 45.8, 45.24, 45.0, 30.9. LRMS (APIMS) m/z 252 (MH$^+$).

1b. 4-Aza-4-(2-methyl-2-(nitrosothio)propyl)tricyclo (5.2.1.0<2,6>)dec-8-ene-3,5-dione To a solution of Example 1a (793 mg, 3.156 mmol) in dichloromethane (23 mL) was added tert-butyl nitrite (750 μL, 650 mg, 6.31 mmol) and the solution was stirred at room temperature for 1 hour in the dark. The reaction mixture was concentrated and the residue chromatographed (ethyl acetate:hexane 2:3) to give the title compound (768.7 mg, 2.738 mmol, 87%). $^1$H NMR (CDCl$_3$) δ6.12 (s, 2H), 4.10 (s, 2H), 3.41 (s, 2H), 3.30 (s, 2H), 1.82 (s, 6H), 1.75 (d, J=8.8 Hz, 1H), 1.57 (d, J=8.8 Hz, 1H). $^{13}$C NMR (CDCl$_3$) δ177.7, 134.7, 56.7, 52.4, 48.0, 47.0, 46.0, 45.8, 45.0, 27.5. LRMS (APIMS) m/z 298 (M$^+$NH$_4$). 99.3% purity by HPLC analysis (Column: Water μBondpack C18; Size: 3.9 mm×150 mm; Solvent A: acetonitrile/0.1% TFA; Solvent B: water/0.1% TFA; Flow rate: 1.0 mL/min; Program: 20% A to 95% A over 20 min.; Detection: 254 nm; Sample: 4.3 mg/mL; Injection volume: 10 μL).

Example 2

4-(1-Methyl-1-(nitrosothio)ethyl)-1,3-oxazolidin-2-one 2a. 2-Amino-3-methyl-3-((2,4,6-trimethoxyphenyl) methylthio)butanoic acid A suspension of 2-amino-3-methyl-3-sulfanylbutanoic acid (D-penicillamine) (5.0 g, 34 mmol) in CH$_2$Cl$_2$ (150 mL) was cooled to 0° C. Trifluoroacetic acid (54 mL, 703 mmol) was added dropwise over a period of 5 minutes. Then 2,4,6-trimethoxybenzyl alcohol (6.64 g, 34 mmol) in CH$_2$Cl$_2$ (137 mL) was added dropwise at 0° C. with stirring. Stirring was continued for 1 hour at 0° C. and 2 hours at room temperature. The solvent was removed in vacuo and the residue was dried under high vacuum for 3 hours. The crude red solid was recrystallized from 1:1:1 CH$_2$Cl$_2$/MeOH/EtOAc to give the title compound as a white solid (10.5 g, 95%). $^1$H NMR (300 MHz, CDCl$_3$) δ6.10 (s, 2H), 3.84 (s, 6H), 3.76 (s, 3H), 3.40–4.10 (m, 3H), 1.69 (s, 3H), 1.23 (s, 3H). LRMS (EI) m/z 330 (MH$^+$).

2b. 2-Amino-3-methyl-3-((2,4,6-trimethoxyphenyl) methylthio)butan-1-ol

To a stirred solution of Example 2a (10.5 g, 32 mmol) in THF (80 mL) was added dropwise lithium aluminum hydride (1 M in THF, 64 mL, 64 mmol) at 0° C. under nitrogen. The resulting solution was stirred at 0° C. for 1 hour and then at room temperature for 2 hours. The excess reducing agent was destroyed carefully by portionwise addition of Na$_2$SO$_4$.OH$_2$O at 0° C. The granular white precipitate was filtered and washed with 30% methanol in CH$_2$Cl$_2$. The combined filtrates were dried over Na$_2$SO$_4$, filtered and evaporated to give the title compound as a yellow oil (7.6 g, 76%) which was used for the next step without further purification. $^1$H NMR (300 MHz, CDCl$_3$) δ6.10 (s, 2H), 3.85 (s, 6H), 3.81 (s, 3H), 3.74 (s, 2H), 3.60–3.80 (m, 2H), 3.37–3.43 (m, 1H), 2.93–2.98 (m, 1H), 1.45 (s, 3H), 1.30 (s, 3H). LRMS (EI) m/z 316 (MH$^+$).

2c. 4-{1-Methyl-1-((2,4,6-trimethoxyphenyl)methylthio) ethyl}-1,3-oxazolidin-2-one A mixture of K$_2$CO$_3$ (0.33 g, 2.4 mmol), diethylcarbonate (50 mL) and the product of Example 2b (7.6 g, 24 mmol) was heated at 100° C. for 24 hours. The solvent was evaporated and the resultant light brown slurry was cooled to room temperature, diluted with CH$_2$Cl$_2$ and filtered to remove the K$_2$CO$_3$. The filtrate was evaporated and the residue was chromatographed on silica gel eluting with 1:1 EtOAc:Hex to give the title compound as a viscous yellow oil (2.6 g, 32%). $^1$H NMR (300 MHz, CDCl$_3$) δ6.13 (s, 2H), 6.07 (bs, 1H), 4.30–4.40 (m, 1H), 4.25–4.28 (m, 1H), 4.03–4.08 (m, 1H), 3.86 (s, 6H), 3.83 (s, 2H), 3.81 (s, 3H), 1.32 (s, 3H), 1.27 (s, 3H). $^{13}$C NMR (75 MHz, CDCl$_3$) δ160.7, 159.5, 158.7, 106.3, 90.9, 66.5, 59.5, 56.0, 55.5, 47.1, 23.8, 22.3, 20.3. LRMS (EI) m/z 342 (MH$^+$), 359 (MNH$_4^+$), 364 (MNa$^+$).

2d. 4-(1-Methyl-1-sulfanylethyl)-1,3-oxazolidin-2-one

The product of Example 2c (2.5 g, 7.3 mmol) was treated with water (2.9 mL), phenol (2.9 g), anisole (2.9 mL) and finally trifluoroacetic acid (36 mL). The resultant solution was stirred at room temperature for 1 hour and the solvent was evaporated to give a yellow oil. The yellow oil was dissolved in $CH_2Cl_2$, washed with saturated sodium bicarbonate, brine and dried over $Na_2SO_4$. The residue after filtration and evaporation of the solvent was chromatographed on silica gel eluting with 0.5:1:1 EtOAc:$CH_2Cl_2$:Hex to give the title compound as a white solid (0.94 g, 80%). mp 124–126° C. $^1H$ NMR (300 MHz, $CDCl_3$) δ6.00–6.10 (bs, 1H), 4.30–4.50 (m, 2H), 3.80–3.84 (m, 1H), 1.69 (s, 1H), 1.36 (s, 3H), 1.32 (s, 3H). $^{13}C$ NMR (75 MHz, $CDCl_3$) δ160.5, 67.3, 62.9, 46.4, 27.5, 27.4. LRMS (EI) m/z 162 ($MH^+$), 179 ($MNH_4^+$). Anal. Calcd for $C_6H_{11}NO_2S$.⅙ EtOAc: C, 45.52; H, 7.07; N, 7.96. Found: C, 45.83; H, 6.86; N, 8.19.

2e. 4-(1-Methyl-1-(nitrosothio)ethyl)-1,3-oxazolidin-2-one

To a solution of tert-butyl nitrite (1.7 mL of 90% solution, 1.48 g, 14.4 mmol) in $CH_2Cl_2$ (2 mL) was added dropwise a solution of Example 2d (0.94 g, 5.8 mmol) in $CH_2Cl_2$ (13 mL) at 0° C. The resulting green solution was stirred at 0° C. for 20 minutes and then at room temperature for 15 minutes in the dark. The residue after evaporation of the solvent was chromatographed on silica gel eluting with 1:4 EtOAc:$CH_2Cl_2$ to give the title compound as a purple-green solid (0.89 g, 80%). mp 65° C. $^1H$ NMR (300 MHz, $CDCl_3$) δ7.42 (bs, 1H), 4.40–4.65 (m, 3H), 1.94 (s, 3H), 1.92 (s, 3H). $^{13}C$ NMR (75 MHz, $CDCl_3$) δ160.5, 67.0, 61.3, 58.1, 25.3, 24.0. LRMS (EI) m/z 191 ($MH^+$), 208 ($MNH_4^+$). Anal. Calcd for $C_6H_{10}N_2O_3S$: C, 37.89; H, 5.30; N, 14.73; S, 16.85. Found: C, 37.97; H, 5.26; N, 14.45; S, 16.78.

Example 3

Infrared Thermographic Measurements

Female white New Zealand rabbits were anaesthetized with pentobarbitol sodium and placed in a supine position on a warming pad. The warming pad was connected to a temperature control unit to maintain the core (rectal) temperature to 38° C. The labia and clitoris were exposed and kept in position by taping the surrounding skin to the nearby abdominal area. The infrared camera (THERMACAM® SC 1000, Inframetrics Inc., North Billerica, Mass.) was focused on the labia and clitoris and the animal was covered with a chamber to maintain the heat loss due to air movement.

After a steady baseline temperature was maintained and recorded for at least 10 minutes the compound (50 μL) was applied to the surface of the labia and clitoris using a syringe and 27 G needle. The compound was formulated in a mixture of dimethyl sulfoxide (25%) and poly(ethylene glycols) (75%). The poly(ethylene glycols) was a mixture of poly(ethylene glycol) 1450 and poly(ethylene glycol) 400 in a ratio of 1:9 respectively.

The images from the infrared camera were electronically transferred to a PC computer and analyzed using TherMonitor 95, version 1.61 (Thermoteknix System Ltd., Mount pleasant,Cambridge, U. K.). Various color scales in the visible wave length are used to depict the temperature change of the recorded images.

Example 4

Figure 2:
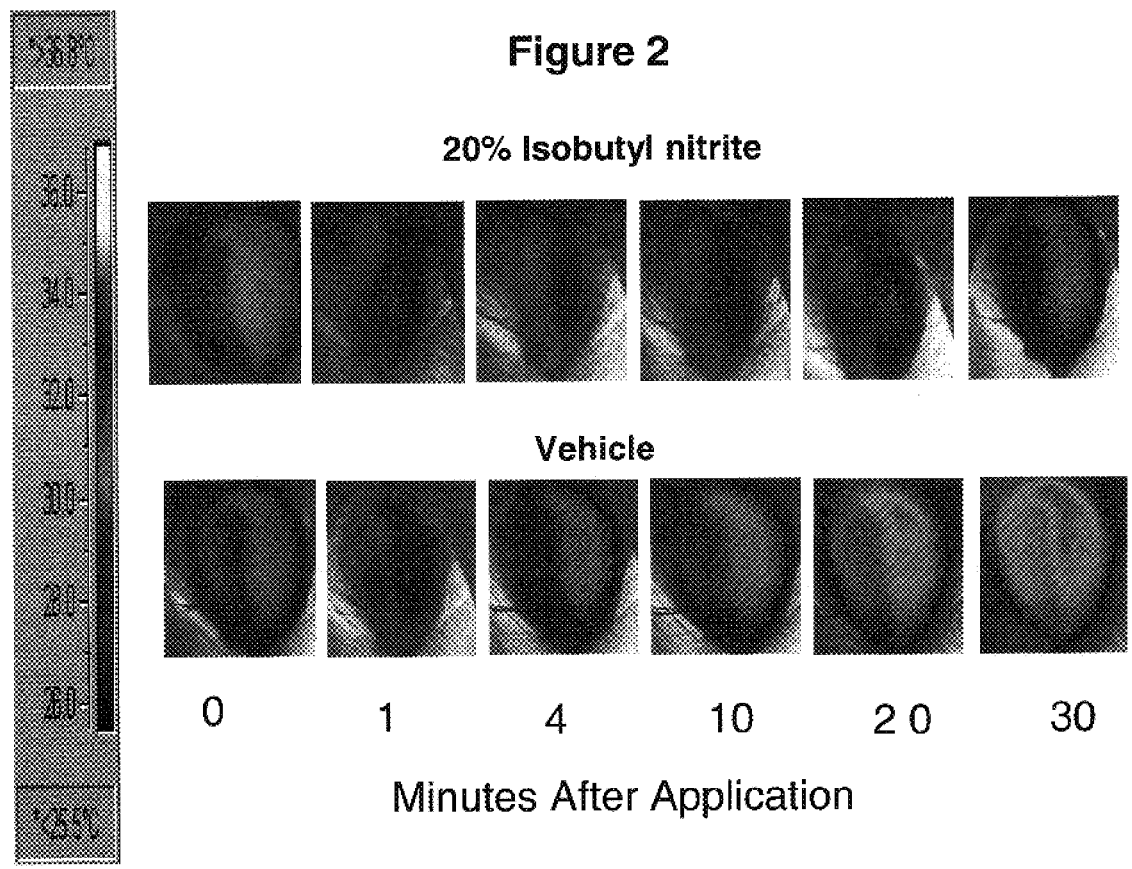
FIG. 2 shows the infrared thermographic images following topical administration of 20% isobutryl nitrate (top panels) or vehicle (bottom panels) to a rabbit vagina and clitoris. The x axis corresponds to time in minutes from just prior to application of isobutryl nitrate or vehicle (0 minutes) to 30 minutes after application of isobutryl nitrate or vehicle. The vertical bar on the left hand side corresponds to the color change for temperatures ranging from 26° C. to 36° C.

Infrared Thermography Measurements Following Topical Administration of Isobutyl Nitrite Infrared thermographic measurements were recorded as described in Example 3. FIGS. 1 and 2 shows the temperature increase of the rabbit genitalia following the topical administration of 10% isobutyl nitrite or vehicle and 20% isobutyl nitrite or vehicle respectively. As can be seen from FIG. 1 (top panels), the temperature of the labia and clitoris changes from ~30° C. prior to the application of the compound to 32° C. following the application of 10% isobutyl nitrite. As can be seen from FIG. 2, application of 20% isobutyl nitrite results in a temperature change from ~31° C. prior to the application of the compound to 34° C. following the application of 20% isobutyl nitrite. The application of the vehicle alone FIGS. 1 and 2 (bottom panels) did not result in a temperature increase.

Example 5

Infrared Thermography Measurements Following Topical Administration of Example 1

Figure 3:
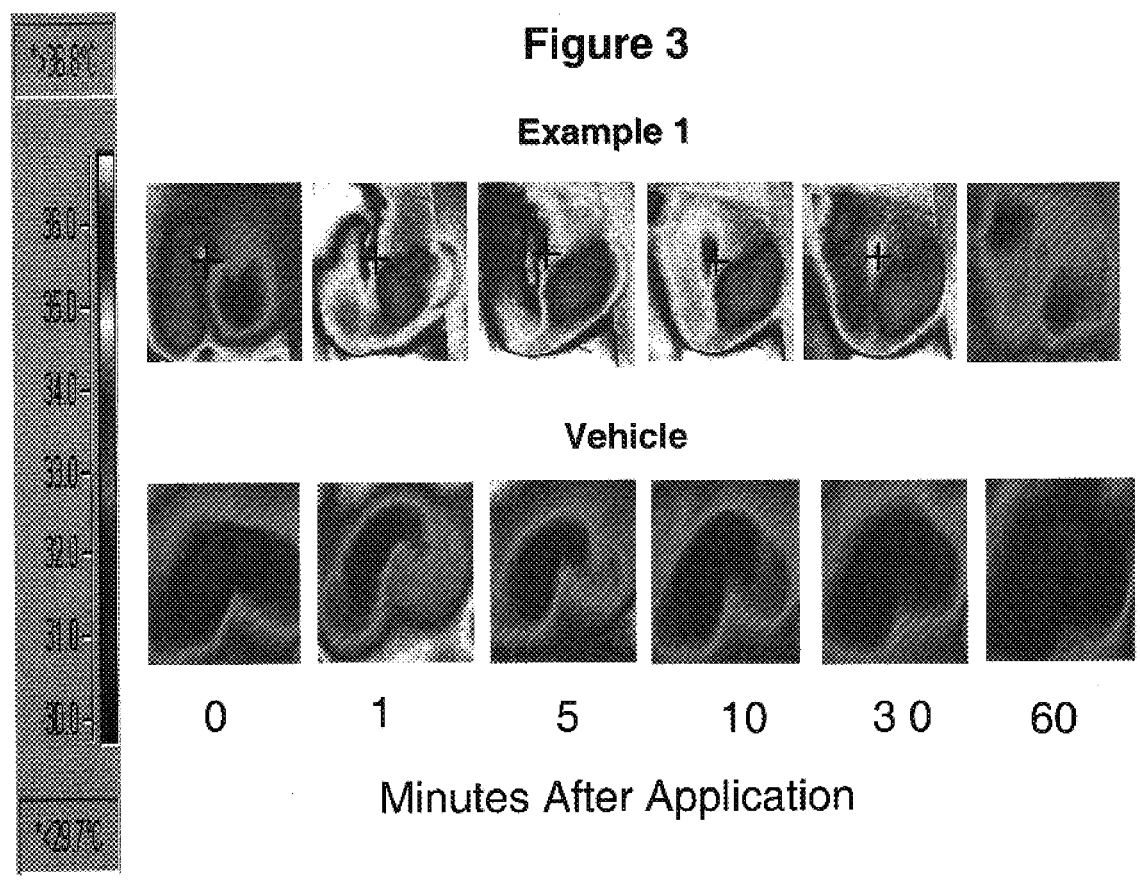
FIG. 3 shows the infrared thermographic images following topical administration of Example 1 (top panels) or vehicle (bottom panels) to a rabbit vagina and clitoris. The x axis corresponds to time in minutes from just prior to application of Example 1 or vehicle (0 minutes) to 60 minutes after application of Example 1 or vehicle. The vertical bar on the left hand side corresponds to the color change for temperatures ranging from 30° C. to 36° C.

Infrared thermographic measurements were recorded as described in Example 3. FIG. 3 shows the temperature change of the rabbit genitalia following the topical administration of Example 1 (5%) or vehicle. As can be seen from FIG. 3 (top panels), the temperature of the labia and clitoris changes from ~32° C. prior to the application of the compound to 35° C. following the application of Example 1. The application of the vehicle alone did not result in a temperature increase FIG. 3 (bottom panels).

Example 6

Infrared Thermography Measurements Following Topical Administration of Example 2

Figure 4:
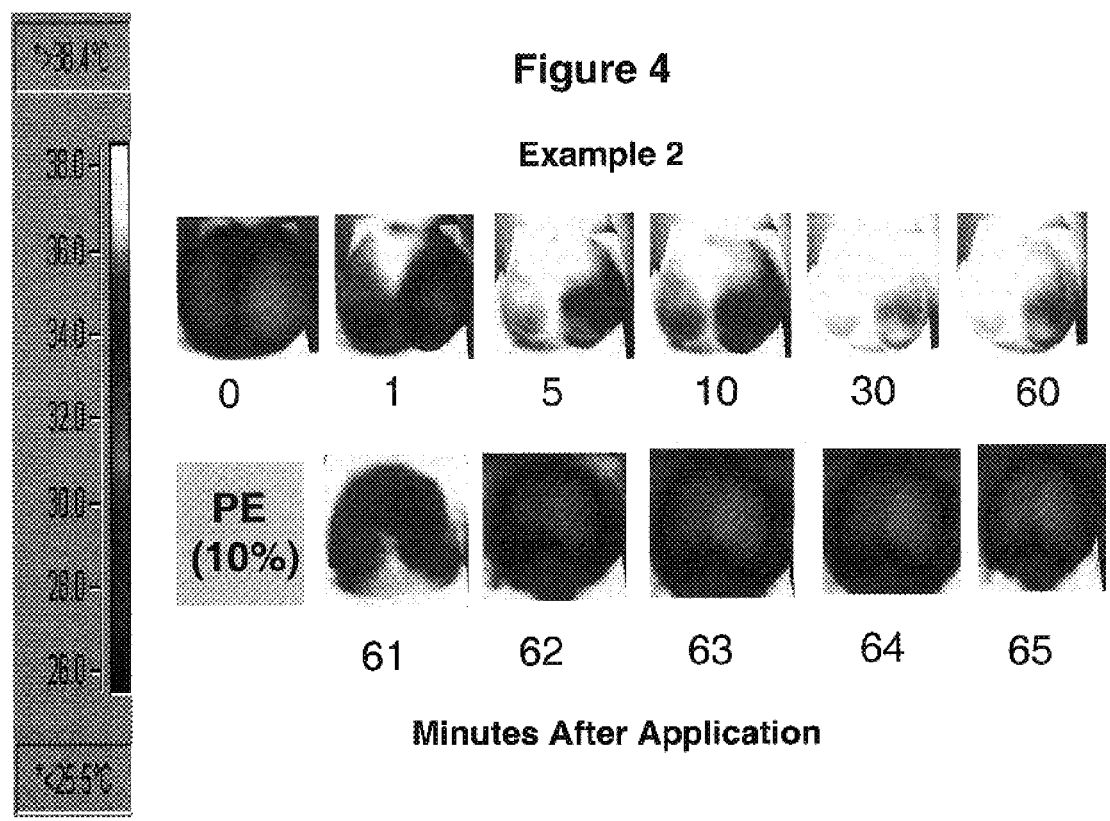
FIG. 4 shows the infrared thermographic images following topical administration of 10% Example 2 (top panels) to rabbit vagina and clitoris. The x axis corresponds to time in minutes from just prior to application of Example 2 (0 minutes) to 60 minutes after application of Example 2. The bottom panels show the effect of administration of 10% phenylephrine (PE 10%, first bottom panel). The x axis corresponds to time in minutes for 5 minutes after the application of phenylephrine from 61 minutes to 65 minutes. The vertical bar on the left hand side corresponds to the color change for temperatures ranging from 26° C. to 38° C.

Infrared thermographic measurements were recorded as described in Example 3. FIG. 4 shows the temperature increase of the rabbit genitalia following the topical administration of Example 2 (10%). As can be seen from FIG. 4 (top panel), the temperature of the labia and clitoris changes from ~32° C. prior to the application of the compound to 36° C. following the application of Example 2. After 60 minutes the vasoconstrictor, phenylephrine (10%), was applied and the temperature monitored for an additional 5 minutes. As can be seen from FIG. 4 (bottom panels), the addition of the vasoconstrictor resulted in a decrease in the temperature from 36° C. to 32° C. The results show that the temperature changes can be used as a measure of vasodilation of the tissue.

Example 7

Preparation of S-nitrosoglutathione

Glutathione (N-(N-L-γ-glutamyl-L-cysteinyl)glycine) (100 g, 0.325 mol) was dissolved in deoxygenated water (200 ml) and 2N HCl (162 ml) at room temperature and then the reaction mixture was cooled to 0° C. With rapid stirring, a solution of sodium nitrite (24.4 g, 0.35 mol) in water (40 ml) was added. Stirring with cooling of the reaction mixture was continued for approximately 1 hour, after which time the pink precipitate which formed was collected by vacuum filtration. The filter cake was resuspended in chilled 40% acetone-water (600 ml) and collected by vacuum filtration. The filter cake was washed with acetone (2×200 ml) and ether (100 ml) and then dried under high vacuum at room temperature in the dark to afford the title compound, N-(N-L-y-glutamyl-S-Nitroso-L-cysteinyl)glycine, as a pink powder. $^1H$ NMR ($D_2O$): δ1.98 (m, 2H), 2.32 (t, 2H), 3.67 (t, 1H), 3.82 (s, 2H), 3.86 (dd, 1H), 3.98 (dd, 1H), 4.53 (m, 1H).

Example 8

Infrared Thermography Measurements Following Topical Administration of Example 7

Figure 5:
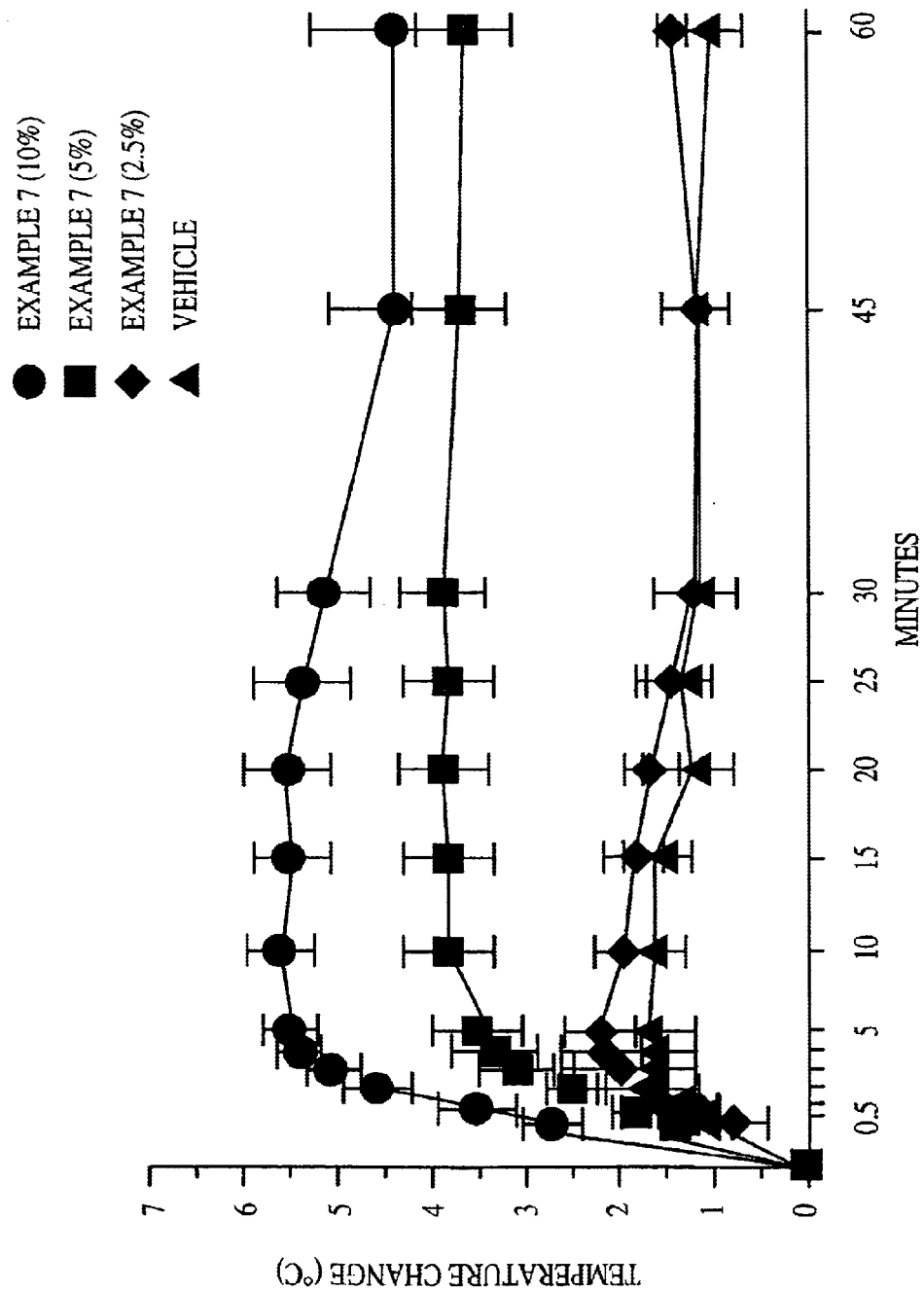
FIG. 5 shows the change in temperature, as measured by infrared thermography, following the topical administration of (a) Example 7 (10%, closed circles); (b) Example 7 (5%, closed squares); (c) Example 7 (2.5%, closed diamonds); or (d) vehicle alone (MIGLYOL, closed trianges); to a rabbit vagina and clitoris. The x axis corresponds to time in minutes. The y axis corresponds to the change in temperature (° C.) after the topical administration of the test compound.

Infrared thermographic measurements were recorded as described in Example 3. FIG. 5 shows the temperature change of the rabbit genitalia following topical application of Example 7 (50 μL, 2.5%), Example 7 (50 μL, 5%), Example 7 (50 μL, 10%) or vehicle (50 μMIGLYOL®). As can be seen from FIG. 5, the temperature of the labia and clitoris increased by 5.5° C. after application of 10% Example 7, and by 3.5° C. after application of 5% Example 7. The application of 2.5% Example 7, or vehicle alone resulted in slight and transient increase of labial clitoral temperature.

Example 9

Laser Doppler Measurements of Labial/Clitoral Blood Flow Following Topical Administration of Example 7

Figure 6:
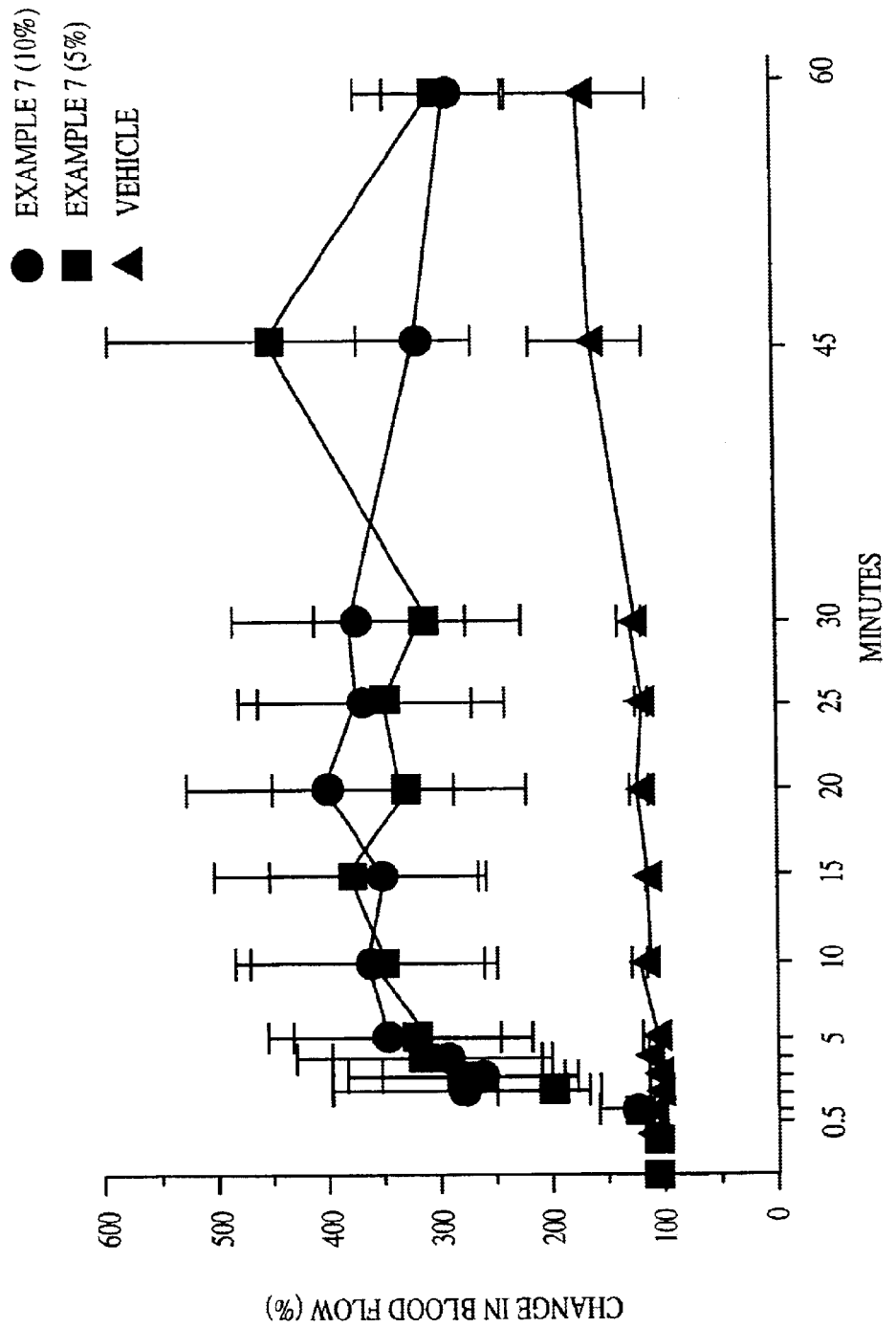
FIG. 6 shows the change in blood flow, as measured by a laser doppler probe, following the topical administration of (a) Example 7 (10%, closed circles); (b) Example 7 (5%, closed squares); or (c) vehicle alone (MIGLYOL®, closed triangles); to a rabbit vagina and clitoris. The x axis corresponds to time in minutes. The y axis corresponds to the change in temperature (° C.) after the topical administration of the test compound.

Female white New Zealand rabbits were anaesthetized with Ketamine/Xylazine mixture and placed in supine position. A laser doppler probe (LASERFLO, BPM 403, Vasamedics, Inc., Minn.) was placed at the labium surface, and after steady baseline blood flow was maintained and recorded for at least 10 minutes, Example 5 (5%, 50 μL), 10% of Example 7 (10%, 50 μL), or vehicle alone (50 μL, MIGLYOL®) was applied to the surface of the labia and clitoris. As seen from FIG. 6, application of Example 7, but not vehicle elicited a sustained (>60 min) increase (4-fold) in labial blood flow as compared to the baseline. The time course for the increase in blood flow (FIG. 6) was very similar to the time course for the increase in labial clitoral temperature (FIG. 5). Hence the measured temperature increase could be the result of the increased blood flow.

The disclosure of each patent, patent application and publication cited or described in the specification is hereby incorporated by reference herein in its entirety.

Although the invention has been set forth in detail, one skilled in the art will appreciate that numerous changes and modifications can be made to the invention without departing from the spirit and scope thereof.

What is claimed is:

1. A method for treating a female sexual dysfunction in a patient in need thereof comprising topically administering to the vagina or vulvar area of the patient a therapeutically effective amount of a composition comprising at least one S-nitrosothiol compound or a pharmaceutically acceptable salt thereof; at least one glyceride; and a pharmaceutically acceptable carrier.

2. The method of claim 1, wherein the S-nitrosothiol compound is S-nitroso-N-acetylcysteine, S-nitroso-captopril, S-nitroso-N-acetylpenicillamine, S-nitro-homocysteine, S-nitroso-cysteine, S-nitroso-glutathione or S-nitroso-cysteinyl-glycine.

3. The method of claim 2, wherein the S-nitrosothiol compound is S-nitroso-glutathione.

4. The method of claim 1, wherein the S-nitrosothiol compound is:

(i) $HS(C(R_e)(R_f))_m SNO$;

(ii) $ONS(C(R_e)(R_f))_m R_e$; or (iii) $H_2N-CH(CO_2H)-(CH_2)_m-C(O)NH-CH(CH_2SNO)-C(O)NH-CH_2-CO_2H$;

wherein m is an integer from 2 to 20; $R_e$ and $R_f$ are each independently a hydrogen, an alkyl, a cycloalkoxy, a halogen, a hydroxy, an hydroxyalkyl, an alkoxyalkyl, an arylheterocyclic ring, an alkylaryl, a cycloalkylalkyl, a heterocyclicalkyl, an alkoxy, a haloalkoxy, an amino, an alkylamino, a dialkylamino, an arylamino, a diarylanilno, an alkylarylamino, an alkoxyhaloalkyl, a haloalkoxy, a sulfonic acid, a sulfonic ester, an alkylsulfonic acid, an arylsulfonic acid, an arylalkoxy, an alkylthio, an arylthio, a cycloalkylthio, a cycloalkenyl, a cyano, an aminoalkyl, an aminoaryl, an aryl, an arylalkyl, an alkylaryl, a carboxamido, a alkylcarboxamido, an arylcarboxamido, an amidyl, a carboxyl, a carbamoyl, a carbamate, an alkylcarboxylic acid, an arylcarboxylic acid, an alkylcarbonyl, an arylcarbonyl, an ester, a carboxylic ester, an alkylcarboxylic ester, an arylcarboxylic ester, a haloalkoxy, a sulfonamido, an alkylsulfonamido, an arylsulfonamido, a sulfonic ester, a urea, a phosphoryl, a nitro, —T—Q , or —(C($R_e$)($R_f$))$_k$—T—Q, or $R_e$ and $R_f$ taken together with the carbons to which they are attached form a carbonyl, a methanthial, a heterocyclic ring, a cycloalkyl group or a bridged cycloalkyl group; Q is —NO or —NO$_2$; and T is independently a covalent bond, a carbonyl, an oxygen, —S(O)$_o$— or N($R_a$)$R_i$—, wherein o is an integer from 0 to 2, $R_a$ is a lone pair of electrons, a hydrogen or an alkyl group; $R_i$ is a hydrogen, an alkyl, an aryl, an alkylcarboxylic acid, an aryl carboxylic acid, an alkylcarboxylic ester, an arylcarboxylic ester, an alkylcarboxamido, an arylcarboxamido, an alkylaryl, an alkylsulfinyl, an alkylsulfonyl, an arylsulfinyl, an arylsulfonyl, a sulfonanildo, a carboxamido, a carboxylic ester, an amino alkyl, an amino aryl, —CH$_2$—C(T—Q)($R_e$)($R_f$), or —(N$_2$O$_2$—)· M$^+$, wherein M$^+$ is an organic or inorganic cation; with the proviso that when $R_i$ is —CH$_2$—C(T—Q)($R_e$)($R_f$) or —(N$_2$O$_2$—)·M; then "—T—Q" can be a hydrogen, an alkyl group, an alkoxyalkyl group, an aminoalkyl group, a hydroxy group or an aryl group.

5. The method of claim 1, wherein the glyceride is a mono glyceride, a diglyceride, a triglyceride, a polyglycolyzed glyceride, or a mixture thereof.

6. The method of claim 1, wherein the glyceride is a mixture of caprylic triglycerides and capric triglycerides, a decanoyl triglyceride, an octanoyl triglyceride, a $C_8$–$C_{12}$ triglyceride, a saturated polyglycolyzed glyceride, a glyceryl caprylate/caprate and PEG-8 (polyethylene glycol) caprylate/caprate complex, a unsaturated polyglycolyzed glyceride, an apricot kernel oil PEG-6 complex, an almond oil PEG-6 complex, a peanut oil PEG-6 complex, an olive oil PEG-6 complex, a corn oil PEG-6 complex, an ethoxylated glyceride, a glyceryl caprylate/caprate PEG-4 complex, or a mixture thereof.

7. The method of claim 1, wherein the composition is in the form of a cream, a spray, a lotion, a gel, an ointment, an emulsion, a foam, a coating for a condom, or a liposome composition.

8. The method of claim 1, further comprising administering to the patient a therapeutically effective amount of at least one vasoactive agent.

9. The method of claim 8, wherein the vasoactive agent is a potassium channel activator, a calcium channel blocker, an α-adrenergic receptor antagonist, a β-blocker, a phosphodiesterase inhibitor, adenosine, an ergot alkaloid, a vasoactive intestinal peptide, a prostaglandin, a dopamine agonist, an opioid antagonist, an endothelin antagonist, a thromboxane inhibitor or a mixture thereof.

10. The method of claim 1, further comprising administering to the patient at least one compound that donates, transfers or releases nitric oxide, elevates endogenous levels of endothelium-derived relaxing factor, stimulates endogenous synthesis of nitric oxide or is a substrate for nitric oxide synthase.

11. The method of claim 10, wherein the at least one compound that donates, transfers or releases nitric oxide, elevates endogenous levels of endothelium-derived relaxing factor, stimulates endogenous synthesis of nitric oxide or is a substrate for nitric oxide synthase is:

(i) a compound that comprises at least one ON—O—, ON—N— or ON—C— group;

(ii) a compound that comprises at least one $O_2N$—O—, $O_2N$—N—, $O_2N$—S— or $O_2N$—C— group;

(iii) a N-oxo-N-nitrosoamine having the formula: $R^1R^2$—N(O—M$^+$)—NO, wherein $R^1$ and $R^2$ are each independently a polypeptide, an amino acid, a sugar, an oligonucleotide, a straight or branched, saturated or unsaturated, aliphatic or aromatic, substituted or unsubstituted hydrocarbon, or a heterocyclic group, and M$^+$ is an organic or inorganic cation.

12. The method of claim 11, wherein the compound comprising at least one ON—O—, ON—N— or ON—C— group is an ON—O-polypeptide, an ON—N-polypepetide, an ON—C— polypeptide, an ON—O-amino acid, an ON—N-amino acid, an ON—C-amino acid, an ON—O-sugar, an ON—N-sugar, an ON—C-sugar, an ON—O-oligonucleotide, an ON—N-oligonucleotide, an ON—C—oligonucleotide, a straight or branched, saturated or unsaturated, substituted or unsubstituted, aliphatic or aromatic ON—O-hydrocarbon, a straight or branched, saturated or unsaturated, substituted or unsubstituted, aliphatic or aromatic ON—N-hydrocarbon, a straight or branched, saturated or unsaturated, substituted or unsubstituted, aliphatic or aromatic ON—C-hydrocarbon, an ON—O-heterocyclic compound, an ON—N-heterocyclic compound or a ON—C-heterocyclic compound.

13. The method of claim 11, wherein compound comprising at least one $O_2N$—O—, $O_2N$—N—, $O_2N$—S— or $O_2N$—C— group is an $O_2N$—O-polypeptide, an $O_2N$—N-polypeptide, an $O_2N$—S-polypeptide, an $O_2N$—C-polypeptide, an $O_2N$—O-amino acid, $O_2N$—N-amino acid, $O_2N$—S—amino acid, an $O_2N$—C-amino acid, an $O_2N$—O-sugar, an $O_2N$—N-sugar, $O_2N$—S-sugar, an $O_2N$—C-sugar, an $O_2N$—O-oligonucleotide, an $O_2N$—N-oligonucleotide, an $O_2N$—S-oligonucleotide, an $O_2N$—C-oligonucleotide, a straight or branched, saturated or unsaturated, aliphatic or aromatic, substituted or unsubstituted $O_2N$—O-hydrocarbon, a straight or branched, saturated or unsaturated, aliphatic or aromatic, substituted or unsubstituted $O_2N$—N-hydrocarbon, a straight or branched, saturated or unsaturated, aliphatic or aromatic, substituted or unsubstituted $O_2N$—S-hydrocarbon, a straight or branched, saturated or unsaturated, aliphatic or aromatic, substituted or unsubstituted $O_2N$—C-hydrocarbon, an $O_2N$—O-heterocyclic compound, an $O_2N$—N-heterocyclic compound, an $O_2N$—S-heterocyclic compound or an $O_2N$—C-heterocyclic compound.

14. The method of claim 10, wherein the at least one compound that donates, transfers or releases nitric oxide, elevates endogenous levels of endothelium-derived relaxing factor, stimulates endogenous synthesis of nitric oxide or is a substrate for nitric oxide synthase is L-arginine, L-homoarginine, N-hydroxy-L-arginine, nitrosated L-arginine, nitrosylated L-arginine, nitrosated N-hydroxy-L-arginine, nitrosylated N-hydroxy-L-arginine, citrulline, ornithine, glutamine, lysine, a polypeptide comprising at least one of these amino acids or an inhibitor of the enzyme arginase.

15. The method of claim 10, wherein the at least one compound that donates, transfers or releases nitric oxide, elevates endogenous levels of endothelium-derived relaxing factor, stimulates endogenous synthesis of nitric oxide or is a substrate for nitric oxide synthase is a NONOate.

* * * * *